US012590958B2

(12) United States Patent
Toldi et al.

(10) Patent No.: US 12,590,958 B2
(45) Date of Patent: Mar. 31, 2026

(54) ASSESSING RESPONSIVENESS OF RHEUMATOID ARTHRITIS PATIENTS TO BIOLOGICAL TREATMENT

(71) Applicant: Navolab Diagnosztika Kft., Szeged (HU)

(72) Inventors: Gergely Toldi, Budapest (HU); Kata Filkor, Salgótarján (HU); Péter Szerémy, Szeged (HU); András Apjok, Szeged (HU); Zoltán Szekanecz, Debrecen (HU)

(73) Assignee: Navolab Diagnosztika Kft., Szeged (HU)

( * ) Notice: Subject to any disclaimer, the term of this patent is extended or adjusted under 35 U.S.C. 154(b) by 1287 days.

(21) Appl. No.: 17/055,835

(22) PCT Filed: May 15, 2019

(86) PCT No.: PCT/HU2019/050025
§ 371 (c)(1),
(2) Date: Nov. 16, 2020

(87) PCT Pub. No.: WO2019/220158
PCT Pub. Date: Nov. 21, 2019

(65) Prior Publication Data
US 2021/0382049 A1      Dec. 9, 2021

(30) Foreign Application Priority Data

May 15, 2018    (EP) ..................................... 18172478
May 30, 2018    (HU) ..................................... 1800184

(51) Int. Cl.
*G01N 33/564*      (2006.01)
*G01N 21/64*      (2006.01)
*G01N 33/50*      (2006.01)

(52) U.S. Cl.
CPC ....... *G01N 33/564* (2013.01); *G01N 21/6428* (2013.01); *G01N 33/505* (2013.01); *G01N 2021/6439* (2013.01); *G01N 2333/705* (2013.01); *G01N 2800/102* (2013.01); *G01N 2800/52* (2013.01)

(58) Field of Classification Search
CPC ............. G01N 33/564; G01N 21/6428; G01N 33/505; G01N 2021/6439; G01N 2333/705; G01N 2800/102; G01N 2800/52
USPC .......................................... 435/7.24; 436/172
See application file for complete search history.

(56) References Cited

U.S. PATENT DOCUMENTS

2017/0335367 A1      11/2017    Barril et al.

FOREIGN PATENT DOCUMENTS

EP          1 882 946 B1      1/2008

OTHER PUBLICATIONS

Szekanecz z et al: "Op0230 multi drug 1-31 resistance (mor) protein activity of activated T lymphocytes is a predictor of biological treatment response in rheumatoid arthritis" Annals of the rheumatic diseases, british medical association, v 75, p. 145, (2016). (Year: 2016).*
Micsik et al ("MDR1 and MRP-1 activity in peripheral blood leukocytes of rheumatoid arthritis patients", Diagnostic Pathology, 2015, 10:216, pp. 1-8) (Year: 2015).*
Lebedeva, Irina V. et al: "Sensitive and Specific Fluorescent Probes for Functional Analysis of the Three Major Types of Mammalian ABC Transporters", PLOS One, Jul. 2011, vol. 6, No. 7, p. e22429.
Micsik, Tamas et al: "Decreased Functional Activity of Multidrug Resistance Protein in Primary Colorectal Cancer", Diagnostic Pathology, Biomed Central Ltd, LO, Apr. 2015, vol. 10, No. 1, p. 26.
Micsik, Tamas et al: "MDR-1 and MRP-1 activity in peripheral blood leukocytes of rheumatoid arthritis patients", Diagnostic Pathology, Dec. 2015, vol. 10, p. 216.
Toldi, G.: "Detection of Multidrug Resistance Activity Using Flow Cytometry as a Diagnostic Tool", Drg Discovery ACC, Liverpool; Oct. 13/14, 2016.
Márki-Zay, J. et al.: "Performance Evaluation of the SOLVO MDQ-Kit", Clin Chem Lab Med., 2012, vol. 50.(8)eA36-eA37.
Bystrom, J. et al: "Response to Treatment with TNFα Inhibitors in Rheumatoid Arthritis Is Associated with High Levels of GM-CSF and GM-CSF+ T Lymphocytes", Clin Rev Allergy Immunol., 2017, vol. 53, No. 2., pp. 265-276.

(Continued)

*Primary Examiner* — Christopher L Chin
(74) *Attorney, Agent, or Firm* — Jason D. Voight

(57)          ABSTRACT

The relates to the field of diagnosis and treatment of Rheumatoid Arthritis, in particular of assessing responsiveness of rheumatoid arthritis patients to biological treatment. In particular the it has been found that measurement of MDR1 and/or MRP1 transport activities in the early phase of or before a bDMARD treatment is appropriate to provide a prediction on the effectiveness or success of bDMARD therapy once csDMARD therapy has failed. Thus, the invention relates to an in vitro diagnostic method for assessing the responsiveness of a sDMARD treated RA patient to bDMARD therapy, wherein preferably the patient is in need of a switch or modification of the sDMARD therapy by measuring transport activities of the above-mention transporters or their composite activities. The invention also relates to use of kits for the methods of the invention and methods for treatment comprising the diagnosis or prediction of the invention.

23 Claims, 6 Drawing Sheets

(56) References Cited

OTHER PUBLICATIONS

Romao, V. C. et al.: "Right drug, right patient, right time: aspiration or future promise for biologics in rheumatoid arthritis?", Arthritis Res Ther, 2017, vol. 19, No. 1, p. 239.

Tsujimura, S. et al., "Disease control by regulation of p. glycoprotein on lymphocytes in patients with rheumatoid arthritis", World J Exp Med, 2015, vol. 5, No. 4., pp. 225-231.

Verheul, M. K. et al.. "Biomarkers for rheumatoid and psoriatic arthritis", Clin Immunol, 2015, vol. 161, No. 1, pp. 2-10.

Wijbrandts, C. A. et al.: "Prediction of Response to Targeted Treatment in Rheumatoid Arthritis", Mayo Clin Proc, 2017, vol. 92, No. 7, pp. 1129-1143.

\* cited by examiner

Responder
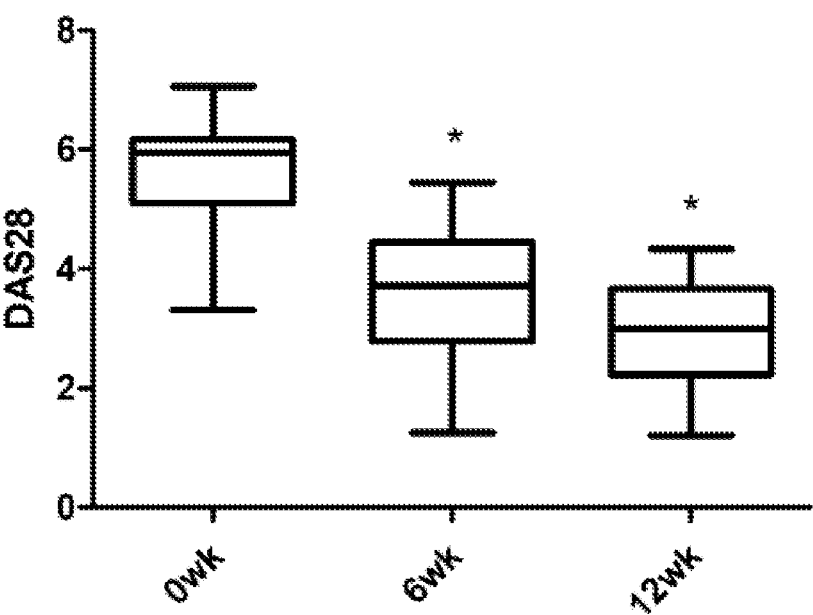
FIGURE 1.A
Non-responder
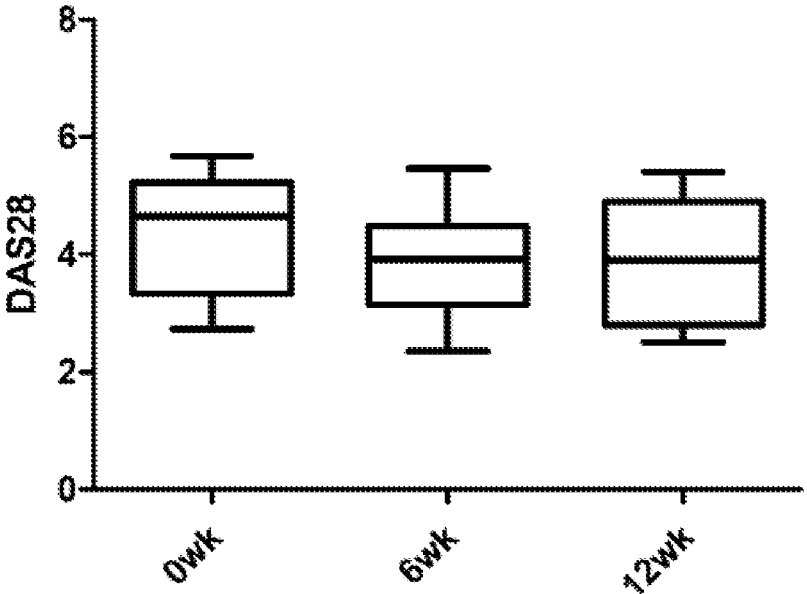
FIGURE 1.B

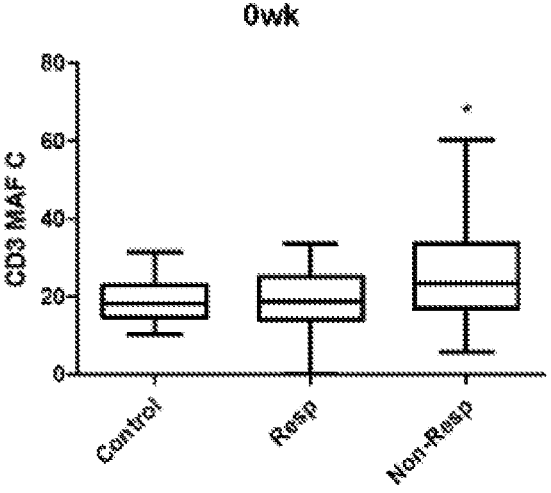
FIGURE 2.A.1
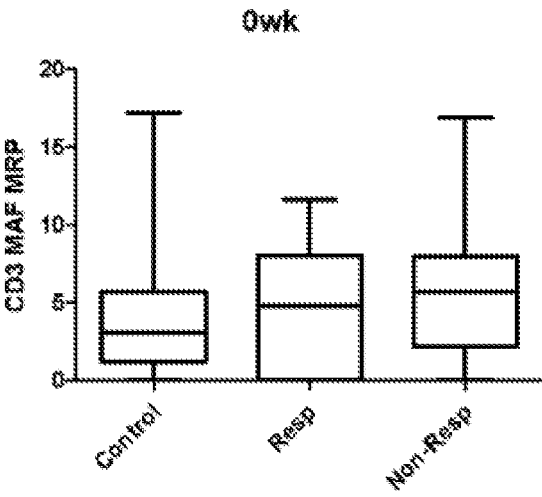
FIGURE 2.A.2
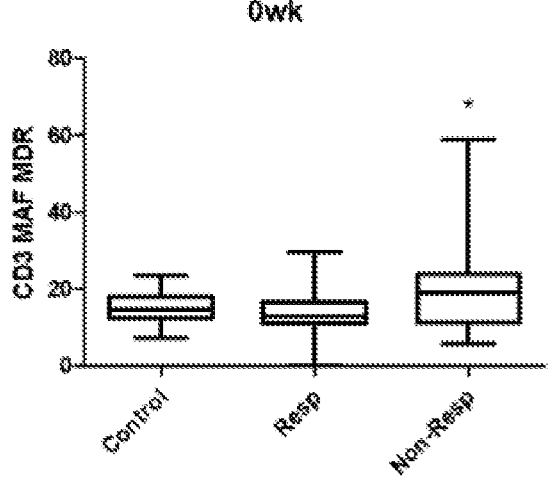
FIGURE 2.A.3
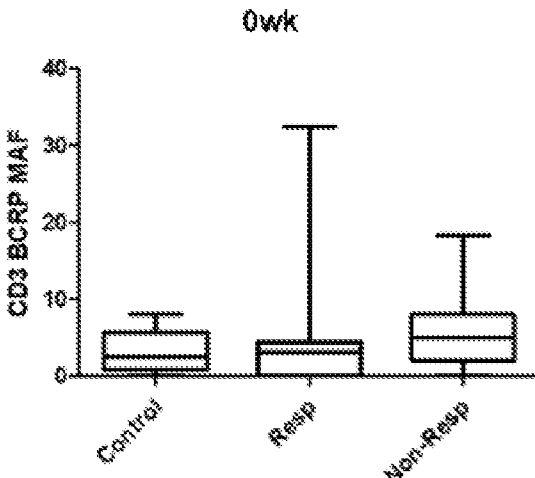
FIGURE 2.A.4

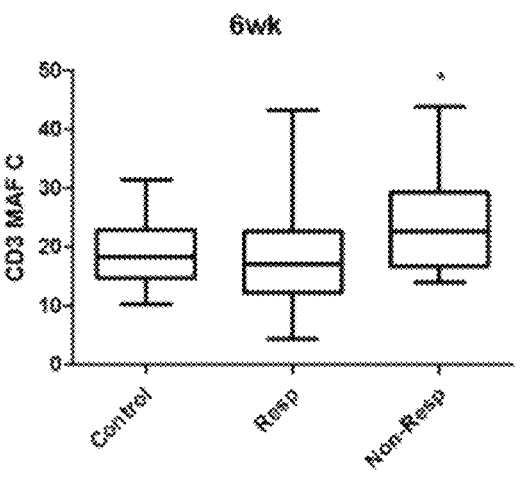
FIGURE 2.B.1
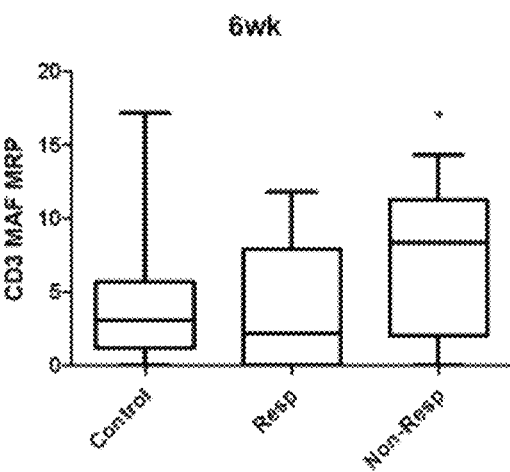
FIGURE 2.B.2
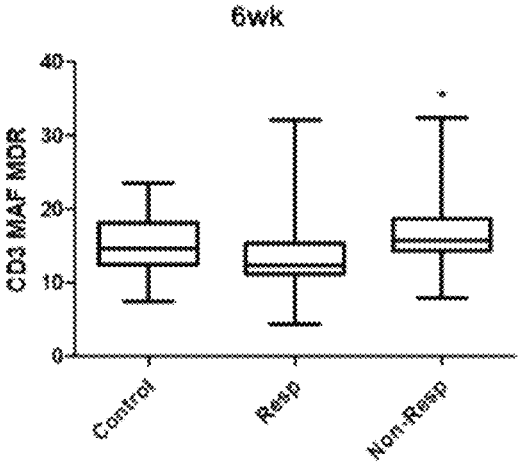
FIGURE 2.B.3
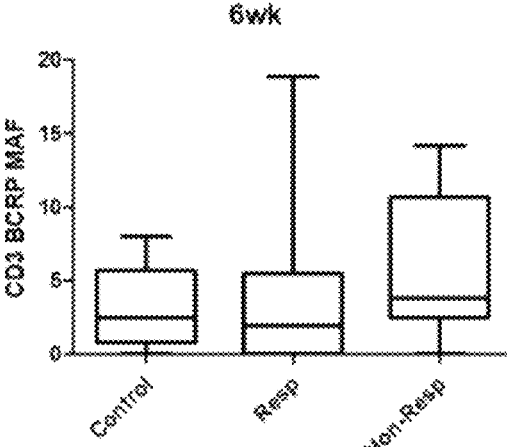
FIGURE 2.B.4

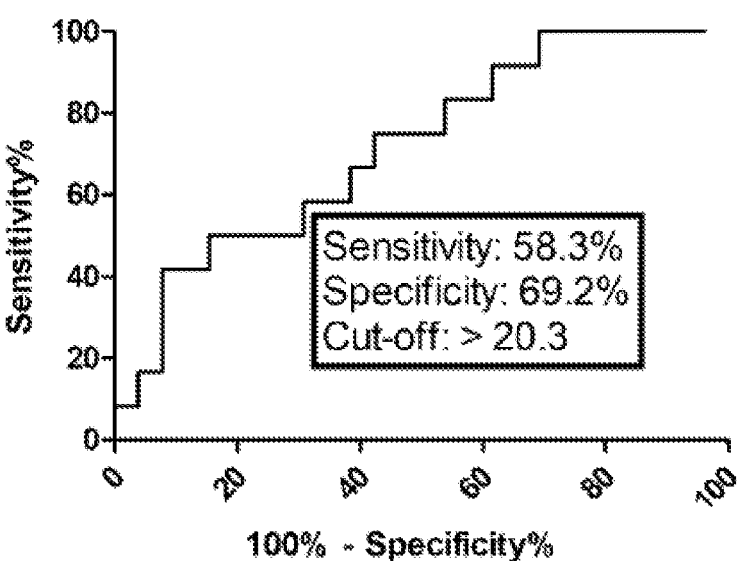
FIGURE 3.A
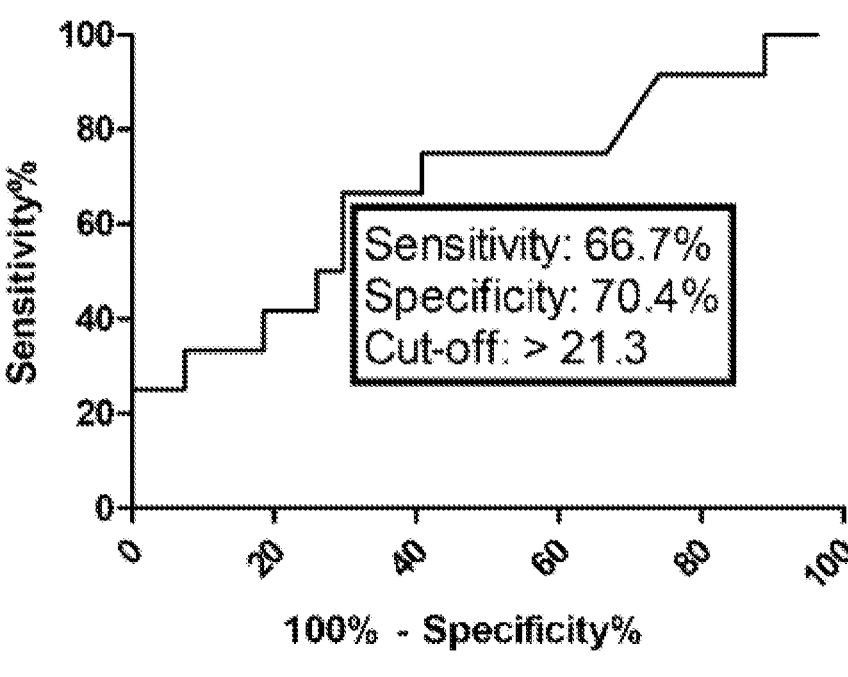
FIGURE 3.B

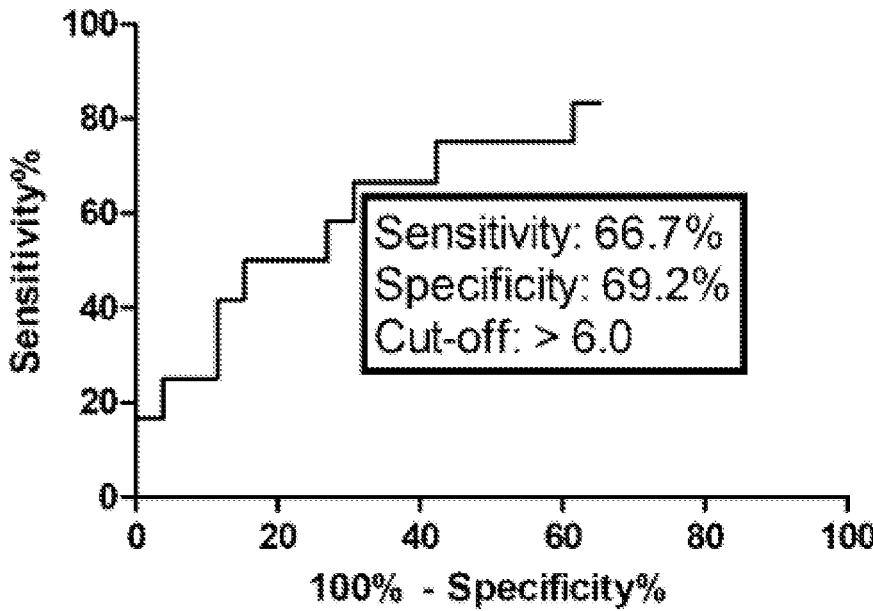
FIGURE 3.C
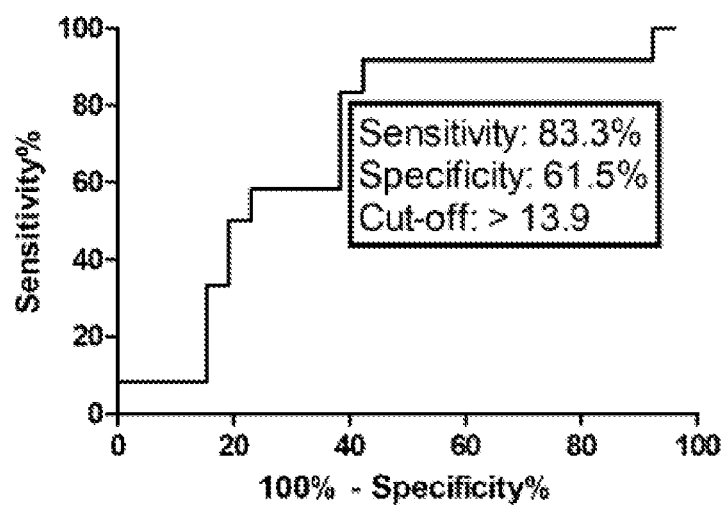
FIGURE 3.D

ROC of CD3 MAF C at 0wk
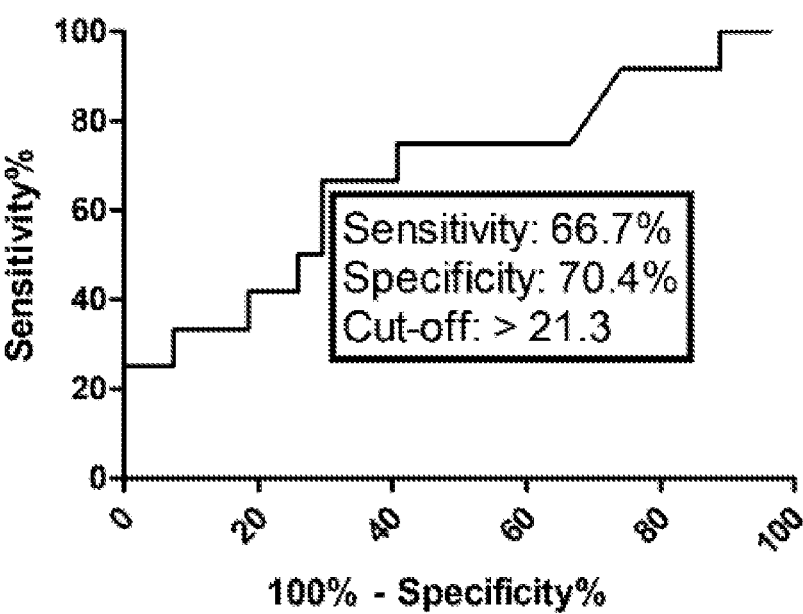
FIGURE 4.A
ROC of CD3 MDR at 0wk
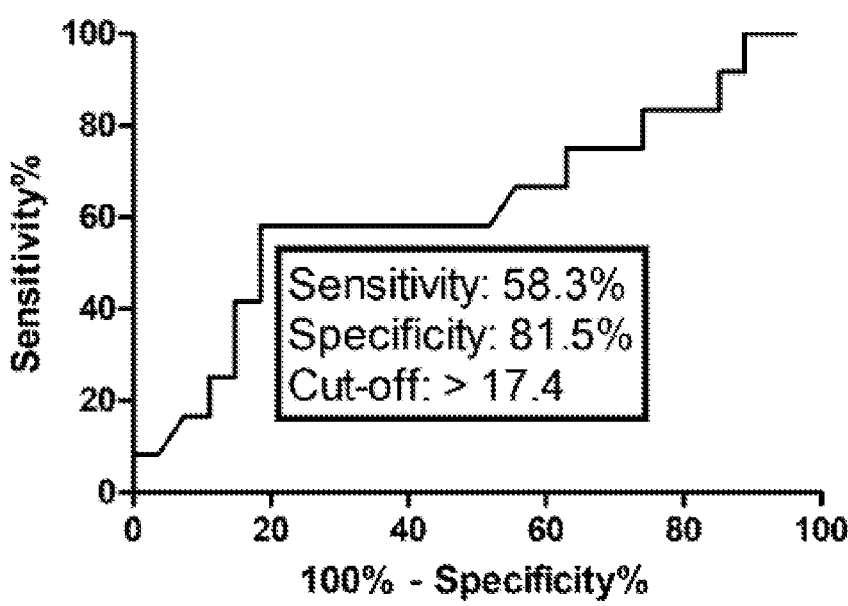
FIGURE 4.B

ASSESSING RESPONSIVENESS OF RHEUMATOID ARTHRITIS PATIENTS TO BIOLOGICAL TREATMENT

This is the national stage of International Application PCT/HU2019/050025, filed May 15, 2019.

FIELD OF INVENTION

The invention relates to the field of diagnosis and treatment of Rheumatoid Arthritis (RA), in particular of assessing responsiveness of RA patients to biological treatment. In particular it has been found that measurement of MDR1 and/or MRP1 transport activities in the early phase of or before a biological disease modifying antirheumatic drug (bDMARD) treatment is appropriate to provide a prediction on the effectiveness or success of bDMARD therapy once classical systemic (cs)DMARD therapy has failed.

BACKGROUND OF INVENTION

Rheumatoid Arthritis

RA affects approximately 0.5-1% of the population (Alamanos and Drosos 2005). The disease is more prevalent in females and it is often appears at the $5^{th}$ decade of the life (Rindfleisch and Muller 2005; Kalliokoski and Niemi 2009). RA is characterized by the overactivation of the immune system and progressive joint destructions (Schett, Hayer et al. 2005). Persistent synovial inflammation finally results in joint and bone malformation (Schett, Hayer et al. 2005; Scott, Wolfe et al. 2010), that drastically cuts down the patient's quality of life (Scott, Pugner et al. 2000).

Biomarkers in RA

Although early diagnosis and immediate, effective therapy are crucial to prevent joint deterioration, functional disability and unfavourable disease outcome (Lima, Azevedo et al. 2013; Lima, Bernardes et al. 2014; Lima, Monteiro et al. 2014), a clear therapeutic target had not yet been defined. Since at the time of diagnosis the disease stage is usually severe and based on the fact that the optimal management of RA is needed within 3-6 months, therefore a very narrow "window of opportunity" is present to achieve remission or at least low disease activity (LDA)(Felson, Smolen et al. 2011; Smolen, Landewe et al. 2017). Therefore, it is very important to predict the efficacy of expensive biologicals at early stage of treatment. Although new generation of drugs is available, there are no validated biomarkers of prognostic use or to predict response to specific therapies (Verheul, Fearon et al. 2015). Although several candidate biomarkers have been investigated, their use is limited either because they require synovial sampling or rely on clinical questionnaires and symptoms besides biomarkers that cannot be objectively measured and validated. For example, a treatment algorithm based on the measurement of serum MRP8/14 levels together with clinical predictors suggested that this may have predictive potential, although this approach was not validated (Wijbrandts and Tak 2017).

Present Treatment Options in RA

In accordance with the current guidelines, methotrexate (MTX) therapy should be started as soon as possible (Smolen, Landewe et al. 2017), except some special cases (Wollenhaupt, Albrecht et al. 2013; Cardiel, Diaz-Borjon et al. 2014; Brenol, Nava et al. 2015; Lau, Chia et al. 2015). Based on the fact that MTX is pivotal in the maintenance of remission, the strict adherence to this particular drug is essential, however, sometimes impossible, since MTX treatment causes serious side effects, which mainly affect the gastrointestinal tract. If there is a known contraindication for MTX, leflunomide or sulfasalazine should be the first-line treatment choice. Three months after starting therapy, a checkup visit should be performed. If the remission was reached, or the patient responds favourably, Phase I therapy should be continued, or the dose of the therapy should be reduced.

If Phase I therapy failed, but the patient falls into good prognostic group, other type of csDMARD; i.e.: leflunomide, or sulfasalazine should be given. If therapy is unsuccessful, biological (b)DMARD (biological originator (bo), or biosimilar (bs), respectively) (anti-TNF, anti-IL6, rituximab) or targeted synthetic (ts) DMARD (e.g. JAK inhibitors) should be given. On the other hand, when Phase I therapy failed and the patient has poor prognostic factors, bDMARD or tsDMARD should be given. When Phase II therapy is failed, another type of bDMARD should be given until complete remission is reached.

Various markers have been proposed to characterize the patient response to treatment with bDMARD therapy. Bystrom J et al. have made cytokine profiling of immune cells and found cells from most anti-TNF responder patients in the current cohort produced higher levels of GM-CSF and TNF pre-treatment than non-responder patients. The authors have suggested that that the disease in responder and non-responder RA patients is likely to be driven/sustained by different inflammatory pathways (Bystrom, Clanchy et al. 2017).

Multidrug Transporters in Health and Disease

Multidrug resistance (MDR-ABC) transporters (MDR1/P-gp/ABCB1; MRP1/ABCC1; BCRP/ABCG2) are important components in the development of drug resistance in malignancies (Gottesman, Fojo et al. 2002) and in autoimmune conditions, such as RA (Marki-Zay, Tauberne Jakab et al. 2013). However, MDR-ABC transporters also transport a variety of endogenic molecules, such as cytokines and chemokines that play important role in the pathogenesis of RA via influencing cell migration, proliferation and inflammation. Therefore, MDR-ABC transporters may also be important biomarkers of disease progression in RA. The assessment of MDR protein activity may help physicians to evaluate how patients will respond to biological treatment and may support the decision whether there is a necessity to modify the treatment.

The most important csDMARDs; including methotrexate (MTX), sulfasalazine, leflunomide and hydroxychloroquine are substrates of MDR proteins. For this reason, MDR activity of RA patients on csDMARD therapy has been extensively studied and the expression, polymorphisms and activity of drug efflux proteins have been linked to therapeutic success of csDMARDs, especially that of MTX. Tsujimura et al. having analyzed MDR1 expression in lymphocytes of patients with RA who had a long history of sDMARD treatment, found an increase in the levels of MDR1 and correlated MDR1 expression with disease activity and steroid treatment [21]. In 2015, Tsujimura and his colleagues also demonstrated that the expression of MDR1 robustly upregulated on the surface of $CD4^{+}$ and $CD19^{+}$ lymphocytes on RA patients as compared with age and gender matched healthy individuals. Furthermore, the expression level of MDR1 was significantly elevated in MTX non-responder patients as compared with responder counterparts. The authors also suggest that treatment by TNF-alpha antagonists probably suppresses transcriptional activation of MDR-1 expression on lymphocytes, and thus inhibition of lymphocyte activation by TNF antagonists "can probably thwart P-gp-mediated treatment resistance in refractory patients with RA" (Tsujimura and Tanaka 2015).

However, little is known about the relation of MDR proteins to therapeutic success of biological (b)DMARDs, such as anti-TNF agents. The literature is divided whether an association can be found among high MDR1 expression and unresponsiveness to MTX therapy and in general the complex inter-relationship among drug resistance, MDR1 and autoimmunity still remains elusive (Picchianti-Diamanti, Rosado et al. 2014).

(b)DMARDs do not enter the cell, and are therefore not substrates of MDR proteins. While endobiotics, such as the cytokines they target are known to interact with these transporters, such mechanisms are far from being understood (Ronaldson, Ashraf et al. 2010; Garcia-Carrasco, Mendoza-Pinto et al. 2015; Ghandadi and Sahebkar 2016).

Based on current ACR and EULAR guidelines, csD-MARD therapy is a first line treatment option for RA patients, in case of non-responsiveness, bDMARD is the second line treatment option (Smolen, Landewe et al. 2017). Thus, it is of particular importance to provide an estimate on patient responsiveness at an early phase or before bDMARD treatment.

A few examples among many efforts to find an appropriate predictor for responsiveness of an anti-TNF-therapy include determining expression level of phosphatidylinositol-4,5-bisphosphate 3-kinase, catalytic subunit delta (PIK3CD) in sample (US20170335367A1), determining the level of Rheumatoid Factor (RF) and/or anti-cyclic citrullinated peptide autoantibody (ACPA) (US20170328897A1), measuring concentration of marker e.g. glycoprotein 130, a cytokine receptor (US20160377612A1), determining baseline serum level of C-X-C motif chemokine 10 and CXCL13 (WO2017181038A1). A different approach measure expression of genes or expression of proteins encoded by the genes is described in WO2012061620A1.

The research group of the present inventors have studied expression of multidrug transporter in blood samples of RA patients and suggested that low MXR/BCRP/ABCG2 and MRP1/ABCC1 transport activities expressed in MAF values on $CD3^+$ T-lymphocytes may predict the need to start biological therapy in RA patients whose symptoms do not improve on classical DMARD treatment and that a further decrease of $CD3^+$ MXR/BCRP/ABCG2 and increase in $CD3^+$ MRP1/ABCC1 MAF at 12 weeks of bDMARD therapy may indicate a favourable therapeutic response to biological therapy (Szekanecz and Koch 2016).

Multi Drug Resistance (MDR) Protein Activity of T Lymphocytes Assessed by Flow Cytometry is a Predictor of Biological Treatment Response in Rheumatoid Arthritis A thorough recent review on potential predictors of response to targeted treatment in rheumatoid arthritis concludes that at present, "no biomarkers are known that can predict response to any biologic DMARD in an individual patient with a high level of certainty" (Wijbrandts and Tak 2017).

A further, still later review also carefully collects results on bDMARD response biomarker research in RA and, while admits that available data may guide treatment decisions to a degree, there are limitations and the authors appear to see that in the future high-throughput omics techniques would be more promising (Romao, Vital et al. 2017).

However, in the prior art no proposal has been made whether measurement of MDR1 and/or MRP1 transport activities in the early phase of or before a bDMARD treatment may be appropriate to provide a prediction on the effectiveness or success of bDMARD therapy once csD- MARD therapy has failed. In general, further predictors of bDMARD treatment are needed in the art.

BRIEF DESCRIPTION OF THE INVENTION

In an aspect the invention relates to an in vitro diagnostic method.

The invention relates to an in vitro diagnostic method for assessing the responsiveness of a sDMARD (preferably csDMARD) treated RA patient to bDMARD therapy, said method comprising the steps of providing a biological sample of said sDMARD (preferably csDMARD) treated RA patient, said sample comprising $CD3^+$ T-lymphocytes from said patient, obtaining one or more transporter activity value(s) by measuring or quantifying transport activity by one or more multidrug transporter(s) selected from the group consisting of MDR1 and MRP1 in the $CD3^+$ T-lymphocytes of said sDMARD (preferably csDMARD) treated RA patient, before or at an initial phase of a bDMARD therapy, by using one or more substrate(s) of MDR1, MRP1 or both MDR1 and MRP1, comparing the one or more transporter activity value(s) with one or more pre-determined threshold transporter activity level(s), wherein each pre-determined threshold transporter activity level is a threshold value for the transport activity of said one or more multidrug transporters and which has been determined using the same one or more substrates, considering said RA patient as a non-responder to the bDMARD therapy when the level of each transporter activity value is above said threshold level, and considering said RA patient as a responder to the bDMARD therapy when the level of each transporter activity value is not higher than said threshold level.

Preferably said threshold transporter activity level is or has been determined by using the one or more substrates by measuring or quantifying transport activity of said one or more multidrug transporters in the $CD3^+$ T-lymphocytes in a (reference) patient group known to be responder to the bDMARD therapy and a (reference) patient group known to be non-responder to the bDMARD therapy, and the transport activity values measured in the responder and non-responder patient groups are analysed (preferably statistically analysed as distributions) to find a threshold level which differentiates between responder transport activity values and non-responder transport activity values.

Preferably the one or more substrates is a substrate of both MDR1 and MRP1 and if transport activity of any of MDR1 and MRP1 is measured separately the other multidrug transporter is inhibited. In a highly preferred embodiment the substrate is a calcein ester, preferably calcein AM.

In a highly preferred embodiment the activity is quantified as a multidrug activity factor (MAF).

Preferably at least the MDR1 activity is measured. In particular embodiment, at least the MRP1 activity is measured. Preferably at least a composite MDR1-MRP1 activity is measured, preferably with a substrate of both MDR1 and MRP1.

Preferably the patient needs a switch or modification of the sDMARD therapy.

In a preferred alternative variant, the invention relates to an in vitro diagnostic method for assessing the responsiveness of a sDMARD (preferably csDMARD) treated RA patient to bDMARD therapy, said method comprising the steps of

5 providing a biological sample of said sDMARD (preferably csDMARD) treated RA patient, said sample comprising CD3$^+$ T-lymphocytes from said patient, obtaining a transporter activity value by measuring transport activity of one or more multidrug transporters comprising at least MDR1, and optionally also MRP1, in the CD3$^+$ T-lymphocytes of said sDMARD (preferably csDMARD) treated RA patient before a bDMARD therapy or in an initial phase thereof, by using an MDR1 substrate which is optionally also the substrate of MRP1, comparing the transporter activity value with a pre-determined threshold transporter activity level, wherein said pre-determined threshold transporter activity level is a threshold value for the transport activity of said one or more multidrug transporters, and which has been determined, using the same MDR1 substrate, considering said RA patient as a non-responder to the bDMARD therapy when the level of the transporter activity value is above said threshold level, and considering said RA patient as a responder to the bDMARD therapy when the level of the transporter activity value is not higher than said threshold level.

Said threshold transporter activity level is or has been determined by using the one or more substrates by measuring or quantifying transport activity of MDR1 and optionally MRP1 in the CD3$^+$ T-lymphocytes in a reference patient group known to be responder to the bDMARD therapy and a reference patient group known to be non-responder to the bDMARD therapy, and the transport activity values measured in the responder and non-responder patient groups are analysed, preferably statistically analysed as distributions, to find a threshold level which differentiates between responder transport activity values and non-responder transport activity values.

Preferably the MDR1 transporter substrate is also a substrate for MRP1. In this embodiment if MDR1 transporter activity is measured or quantified separately MRP1 is inhibited. If the transporter activity comprises activities of both MDR1 and MRP1, the two transporters are not differentiated by inhibition and a composite activity value is obtained.

In a highly preferred embodiment the substrate is a calcein ester, preferably calcein AM.

In a highly preferred embodiment the activity is quantified as a multidrug activity factor (MAF).

Preferably the transport activity of one or more multidrug transporters is a transport activity of MDR1.

Preferably the transport activity of MDR1 is measured by an MDR1 substrate is specific to MDR1 or an MDR1 substrate which is the substrate of at least one other multidrug transporter which is inhibited in the measurement by an inhibitor of said at least one other multidrug transporter (e.g. with an inhibitor which does not inhibit MDR1 or with an inhibitor specific to the least one other multidrug transporter).

In a preferred embodiment the transport activity of one or more multidrug transporters is a composite transport activity of MDR1 and MRP1. Preferably the transport activity of MDR1 is measured by an MDR1 substrate which is also the substrate of MRP1.

In a preferred alternative variant, the invention relates to an in vitro diagnostic method of the invention for assessing the responsiveness of a sDMARD (preferably csDMARD) treated RA patient to bDMARD (bo or bs) therapy, wherein the sDMARD treated RA patient is in need of a switch or modification of the therapy, said method comprising the steps of providing a biological sample of said sDMARD (preferably csDMARD) treated RA patient, said sample comprising lymphocytes from said patient, said lymphocytes including at least CD3$^+$ T-lymphocytes, i.e. said sample is a lymphocyte containing biological sample, measuring, as a transporter activity, at least a composite transporter activity of MDR1 and MRP1 transporter proteins (composite transporter activity, preferably MAF$_C$) in CD3$^+$ T-lymphocytes of said RA patient before starting bDMARD therapy, or at an initial phase of said bDMARD therapy at the latest, thereby obtaining a value for the composite MDR1 MRP1 transporter activity (composite MDR1 MRP1 transporter activity value), comparing the composite MDR1 MRP1 transporter activity value (preferably (MAF$_C$) with a pre-determined threshold transporter activity level, wherein said pre-determined threshold transporter activity level is a threshold value for the composite MDR1 MRP1 transporter activity, and which has been determined by a test in which the (reference) patient group known to be responder to the bDMARD therapy and the (reference) patient group non-responder to the bDMARD therapy have composite MDR1 and MRP1 transporter activities with different statistical distributions, and thus can be or are differentiated based on their composite MDR1 and MRP1 transporter activity, considering said RA patient as a non-responder to the bDMARD therapy when the level of the composite transporter activity is above said threshold level, and considering said RA patient as a responder to the bDMARD therapy when the level of the composite transporter activity is not higher than said threshold level.

In the method of the invention preferably the sDMARD treated RA patient needs a switch or modification of the therapy.

In the method of the invention preferably said biological sample is a leukocyte containing biological sample wherein the leukocytes comprise lymphocytes, preferably a blood sample. Said lymphocytes include CD3$^+$ T-lymphocytes.

In the method of the invention preferably measuring in particular, comprises or includes quantifying of transport activity.

In a preferred embodiment MDR1 activity, MRP1 activity and composite MDR1 and MRP1 activity are each measured and the patients are considered as non-responders if each of the transporter activity values are above threshold, and responders if each of the transporter activity values are not higher than the above threshold.

In the method of the invention preferably the initial phase of the bDMARD therapy means that the method is carried out in the first 8 weeks, preferably in the first 7 or 6 weeks, or preferably the first 4 weeks or highly preferably in the first two weeks of or in the first week of the bDMARD therapy.

In particular, in an alternative wording, the in vitro (diagnostic) method is for determining predisposition of a sDMARD treated RA patient to respond (or not) to bDMARD therapy. In particular, the in vitro (diagnostic) method is for predicting the expectable success or effectiveness of a sDMARD treated RA patient to respond to bDMARD therapy.

In particular, a transporter activity value is obtained by measuring transport activity of MDR1 or MRP1 or a composite of the transport activities of MDR1 and MRP1.

In a highly preferred embodiment the method of any of claim 1 wherein the threshold value is obtained by an ROC analysis.

In a particular embodiment the responder and non-responder patient groups are established by a DAS28 score value.

In a preferred embodiment in the in vitro diagnostic method of the invention the bDMARD therapy is selected from the group consisting of
  anti-TNF therapy (in particular, a monoclonal antibody against TNF),
  T-cell activation inhibitor therapy, e.g. by a costimulation inhibitor, preferably a protein, e.g. fusion protein, binding to CD80 and CD86 molecules (in particular, abatacept),
  anti-B-lymphocyte proliferation therapy (in particular, rituximab),
  anti-IL6 therapy, preferably an IL-6 receptor blocker (in particular tocilizumab, sarilumab) or preferably an IL-6 inhibitor (in particular clazakizumab, sirukumab).

Preferably the bDMARD therapy is anti-TNF therapy or a T-cell activation inhibitor therapy, highly preferably the bDMARD therapy is anti-TNF therapy.

Preferably the anti-TNF therapy may comprise the administration of any of the following drugs:
  adalimumab, certolizumab pegol, etanercept, golimumab, infliximab as boDMARD and their biosimilars. In a particular preferred embodiment of the method of the invention if the patient is assessed to be non-responsive to an anti-TNF therapy or a T-cell activation inhibitor therapy (preferably an anti-TNF therapy), then a different bDMARD therapy selected from
  anti-B-lymphocyte proliferation therapy (for example rituximab),
  anti-IL6 therapy (for example tocilizumab)
which is considered as a modified therapy.

In a particular preferred embodiment, if the patient is assessed to be non-responsive to a bDMARD therapy, including an anti-TNF therapy or a T-cell activation inhibitor therapy, then a different tsDMARD is considered as a modified therapy.

In a preferred embodiment of the method of the invention measuring the transporter activity comprises
  contacting at least the CD3$^+$ T-lymphocytes in the biological sample with the one or more transporter substrate(s), said substrate being a derivative of a detectable fluorescent compound, and wherein said derivative is taken up by at least the CD3$^+$ T-lymphocytes and is hydrolyzed into said fluorescent compound in the cells, wherein said fluorescent compound is not transportable by MDR1 or MRP1 or by neither MDR1 nor MRP1 or transportable to a significantly lesser extent than the derivative, preferably the ester derivative, and
  measuring fluorescence in the CD3$^+$ T-lymphocytes, preferably after labelling them with fluorochrome-conjugated anti-CD3 antibodies,
  obtaining or calculating the transport activity value from the fluorescence in the CD3$^+$ T-lymphocytes.

Preferably measurement is carried out by flow cytometry.

In a preferred embodiment at least MDR1 activity is measured.

In a preferred embodiment, a composite transporter activity is measured, preferably a composite MDR1+MRP1 activity.

In an embodiment, the CD3$^+$ T lymphocytes are collected before transporter activity is measured and thus transporter activity is measured selectively in the CD3$^+$ T lymphocytes.

In another embodiment, the transporter substrate is added to the cells before collecting the CD3$^+$ T lymphocytes (from the biological sample, preferably blood sample) and said CD3$^+$ T lymphocytes are labelled with fluorescently labelled antibodies and fluorescence of the substrate is thus measured in the CD3$^+$ T-lymphocytes.

In appropriate embodiments said derivative is a transportable substrate for both MDR1 and MRP1.

Preferably the MDR1 transporter substrate is added to the biological sample.

In a preferred embodiment the measuring or quantifying the transport activity comprises
  contacting at least the CD3$^+$ T-lymphocytes in the biological sample with an ester derivative of a detectable fluorescent compound, preferably a calcein ester, wherein said derivative is taken up by at least the CD3$^+$ T-lymphocytes and is hydrolyzed into said fluorescent compound in the cells, wherein said fluorescent compound is neither transportable by MDR1 nor MRP1 or transportable to a significantly lesser extent than the ester derivative, and
  measuring fluorescence in the CD3$^+$ T-lymphocytes, preferably after labelling them with fluorochrome-conjugated anti-CD3 antibodies,
  obtaining the composite transporter activity (preferably MAF$_C$) value from the fluorescence in the CD3$^+$ T-lymphocytes.

In a highly preferred embodiment the substrate, preferably the detectable fluorescent ester compound is calcein and/or measuring transport activity is based on the difference between the fluorescence of the detectable fluorescent compound in the cells measured in the presence of an inhibitor, preferably a selective inhibitor, of the multidrug transporters and the fluorescence measured in absence of said inhibitor. Preferably the measurement is carried out by flow cytometry.

Preferably, the fluorescence of the detectable fluorescent compound in the cells measured in the presence of an inhibitor of MDR1 and MRP1 of the multidrug transporters and/or the fluorescence is measured in the presence of a specific MRP1 inhibitor wherein MDR1 is not inhibited. Preferably the MDR1 transporter activity (value) is calculated as an MDR activity factor (MAF$_{MDR1}$) and preferably the MRP1 transporter activity (value) is calculated as an MRP1 activity factor (MAF$_{MRP1}$).

Preferably, the fluorescence of the detectable fluorescent compound in the cells measured in the presence of an inhibitor of MDR1 and MRP1 of the multidrug transporters and the fluorescence measured in absence of said inhibitor; wherein preferably the (quantitative) composite MDR1 MRP1 transporter activity (value) is a composite MDR activity factor (MAF$_C$).

In a preferred embodiment of the methods wherein transporter activity is quantified as a MAF value the biological sample is blood and the MDR1 substrate is calcein and the MDR1 transporter activity (value) threshold level is calculated as an MDR activity factor for MDR1 (MAF$_{MDR1}$) and said threshold (in MAF percentage) is between 15 to 19, preferably 16 to 19 or 16 to 18, more preferably between 17 to 19 or 17 to 18. In a further preferred embodiment the biological sample is blood and the MDR1 substrate is calcein, and the MDR1 transporter activity (value) threshold level is calculated as an MDR activity factor (MAF$_{MDR}$) and said RA patient is considered as a non-responder to biological therapy wherein the level of $\text{MAF}_{MDR}$ is above a $\text{MAF}_{MDR}$ threshold from 15 to 19, preferably 16 to 19 or 16 to 18, more preferably between 17 to 19 or 17 to 18.

In a preferred embodiment of the methods wherein the biological sample is blood and the MDR1 substrate is calcein and the MDR1 transporter activity (value) threshold level is calculated as a composite. The cumulative MDR activity factor for MDR1 and MRP1 ($\text{MAF}_C$) and said threshold is between 19 to 23, preferably 20 to 22 more preferably 21.3. In a further preferred embodiment the biological sample is blood and MDR1 substrate is calcein and the MDR1 transporter activity (value) threshold level is calculated as a composite MDR activity factor for MDR1 and MRP1 ($\text{MAF}_c$) and said RA patient is considered as a non-responder to biological therapy wherein the level of MAFc is above a MAFc threshold from 19 to 23, preferably 21.3.

In a further variant of the method a further measurement of a transporter activity as defined above is also performed. Such measurement may be performed after the above defined one or more measurement. Such measurement may provide additional information about the responsiveness of the patient for the bDMARD therapy.

In an embodiment said sDMARD-treated RA patient has been also treated by bDMARD therapy, said method additionally comprising providing a further biological sample of said sDMARD-treated RA patient between weeks 4 and 7 of the bDMARD therapy, obtaining one or more further transporter activity value(s) by measuring transport activity by one or more multidrug transporter(s) selected from the group consisting of MDR1 and MRP1 in the CD3$^+$ T-lymphocytes of said sDMARD (preferably csDMARD) treated RA patient between weeks 4 and 7 of the bDMARD therapy, by using one or more substrate(s) of MDR1, MRP1 or both MDR1 and MRP1, comparing one or more further transporter activity value(s) with one or more pre-determined threshold transporter activity level(s), wherein each pre-determined threshold transporter activity level is a threshold value for the transport activity of said one or more multidrug transporters and which has been determined using the same one or more substrates, as defined above, considering said RA patient as a non-responder to the biological therapy wherein the level of each transporter activity value is above said each threshold level, and considering said RA patient as a responder to the biological therapy wherein the level of the MDR1 transporter activity value is not higher than said each threshold level.

Preferably, the bDMARD therapy is a bDMARD therapy as defined above or herein.

Preferably measuring/quantifying transporter activity of transporter protein is carried out as defined in any of the paragraphs as defined above for the transport activity measurement.

In a highly preferred embodiment the detectable fluorescent ester compound is calcein ester and/or the (quantitative) composite transporter activity value is based on the difference between the fluorescence of the detectable fluorescent compound in the cells measured in the presence of an inhibitor of the multidrug transporters and the fluorescence measured in absence of said inhibitor. Preferably the (quantitative) transporter activity (value) is MAF value.

In a highly preferred embodiment in measurement or quantifying step, said RA patient is considered as a non-responder to biological therapy wherein upon a measurement between 4 to 7 weeks preferably at about 6 weeks of the bDMARD therapy at least the MDR1 activity is measured, and the transporter activity value is $\text{MAF}_{MDR1}$ value, and said RA patient is considered as a non-responder to biological therapy wherein the level of $\text{MAF}_{MDR1}$. is above a $\text{MAF}_{MDR1}$ threshold from 12 to 15, preferably from 13 to 14, more preferably above a threshold of about 13.9;

at least the MRP1 activity is measured, and the transporter activity value is $\text{MAF}_{MRP1}$ value, and said RA patient is considered as a non-responder to biological therapy wherein the level of $\text{MAF}_{MDR1}$. is above a $\text{MAF}_{MDR1}$ threshold from 5 to 7, preferably from 5.5 to 6.5, more preferably above a threshold of about 6.0.

at least a composite activity is measured, and the transporter activity value is $\text{MAF}_C$ value, and said RA patient is considered as a non-responder to biological therapy wherein the level of $\text{MAF}_C$. is above a $\text{MAF}_{MDR1}$ threshold from 18 to 22, preferably from 19 to 21, more preferably above a threshold of about 20.3.

In a further embodiment the threshold values are set above any of the value as defined above thereby increasing the Preferably the biological sample is blood sample.

Preferably the patient is a mammal, preferably a human.

In a preferred embodiment MDR1 activity, MRP1 activity and composite MDR1 and MRP1 activity are each measured in this stage and the patients are considered as non-responders if each of the transporter activity values are above threshold, and responders if each of the transporter activity values are not higher than the above threshold.

In a further aspect the invention relates to a method for therapy including assessing the responsiveness of a sDMARD (preferably csDMARD) treated RA patient to bDMARD therapy said method comprising the steps of providing a biological sample of said sDMARD (preferably csDMARD) treated RA patient, said sample comprising CD3$^+$ T-lymphocytes from said patient, obtaining one or more transporter activity value(s) by measuring transport activity by one or more multidrug transporter(s) selected from the group consisting of MDR1 and MRP1 in the CD3$^+$ T-lymphocytes of said sDMARD (preferably csDMARD) treated RA patient, before or at an initial phase of a bDMARD therapy, by using one or more substrate(s) of MDR1, MRP1 or both MDR1 and MRP1, comparing the one or more transporter activity value(s) with one or more pre-determined threshold transporter activity level(s), wherein each pre-determined threshold transporter activity level is a threshold value for the transport activity of said one or more multidrug transporters and which has been determined using the same one or more substrates, considering said RA patient as a non-responder to the bDMARD therapy when the level of each transporter activity value is above said threshold level and applying alternative therapy, in particular, an alternative csDMARS therapy or, preferably a tsDMARD therapy;

considering said RA patient as a responder to the bDMARD therapy when the level of each transporter activity value is not higher than said threshold level and applying a bDMARD therapy.

Preferably the therapy comprises any of the diagnostic methods for assessing the responsiveness of a sDMARD (preferably csDMARD) treated RA patient to bDMARD therapy as defined above.

Preferably the bDMARD therapy is as defined above.

In particular, the bDMARD therapy is selected from the group consisting of anti-TNF therapy (in particular, a monoclonal antibody against TNF), T-cell activation inhibitor therapy, preferably a protein, e.g. fusion protein, binding to CD80 and CD86 molecules (in particular abatacept), costimulation inhibitor (in particular abatacept);

anti-B-lymphocyte proliferation therapy (in particular rituximab), anti-IL6 therapy, preferably an IL-6 receptor blocker (in particular tocilizumab, sarilumab) or preferably an IL-6 inhibitor (in particular clazakizumab, sirukumab).

Preferably the bDMARD therapy is anti-TNF therapy or a T-cell activation inhibitor therapy, highly preferably the bDMARD therapy is anti-TNF therapy.

Preferably the anti-TNF therapy may comprise the administration of any of the following drugs: adalimumab, certolizumab pegol, etanercept, golimumab, infliximab as boDMARD and their biosimilars. In a particular, preferred embodiment if the patient is assessed to be non-responsive to an anti-TNF therapy or a T-cell activation inhibitor therapy, preferably an anti-TNF therapy, then a different bDMARD therapy selected from anti-B-lymphocyte proliferation therapy, anti-IL6 therapy (for example tocilizumab), which is considered as a modified therapy.

In a particular preferred embodiment, if the patient is assessed to be non-responsive to a bDMARD therapy, including an anti-TNF therapy or a T-cell activation inhibitor therapy, then a different tsDMARD is considered as a modified therapy.

Preferably the bDMARD therapy is anti-TNF therapy.

Preferably the measuring or quantifying the multidrug transporter activity, in particular, the MDR1 activity, MRP1 activity and/or the composite MDR1 MRP1 transporter activity is carried out as defined above.

In a further aspect the invention relates to a use of a kit for assessing the responsiveness of a sDMARD (preferably csDMARD) treated RA patient to bDMARD therapy before or at an initial phase of the bDMARD therapy, or for a purpose as defined herein, by obtaining one or more transporter activity value(s) by measuring transport activity by one or more multidrug transporter(s) selected from the group consisting of MDR1 and MRP1 in the CD3$^+$ T-lymphocytes of said sDMARD (preferably csDMARD) treated RA patient, wherein said RA patient is considered as a non-responder to the bDMARD therapy when the level of each transporter activity value is above a respective threshold level, or for a purposed, and considering said RA patient as a responder to the bDMARD therapy when the level of each transporter activity value is not higher than a respective threshold level, said kit comprising one or more substrate(s) of MDR1, MRP1 or both MDR1 and MRP1 for the measuring of the respective transporter activity said substrate being taken up by CD3$^+$ T-lymphocytes once contacted with them in a biological sample, wherein preferably said substrate is detectable, preferably fluorescent, label for CD3$^+$ T-lymphocytes, and preferably inhibitor for MRP1 and/or, inhibitor for MDR1.

Preferably the kit as defined above also comprises instructions to carry out the method of the invention.

In a preferred embodiment said use of the kit is for assessing the responsiveness of a sDMARD (preferably csDMARD) treated RA patient to bDMARD therapy before or at an initial phase of the bDMARD therapy as defined above, for use in a method as defined herein or above or in a method according to of any of the in vitro diagnostic methods as defined above, wherein said kit comprises, a substrate for MDR1 and MRP1 for the measuring of a composite MDR1 and MRP1 transport activity, said substrate being taken up by leukocytes (preferably CD3$^+$ T-lymphocytes once contacted), in a biological sample, wherein preferably said substrate is detectable, preferably fluorescent, label for CD3$^+$ T-lymphocytes, preferably a CD3$^+$ T-lymphocyte specific antibody, and preferably inhibitor for MRP1, inhibitor for one or more other multidrug transporter.

In an embodiment the kit also comprises an inhibitor for BCRP.

Preferably said threshold transporter activity level is or has been determined by using the one or more substrates by measuring/quantifying transport activity of said one or more multidrug transporters in the CD3$^+$ T-lymphocytes in a (reference) patient group known to be responder to the bDMARD therapy and a (reference) patient group known to be non-responder to the bDMARD therapy, and the transport activity values measured in the responder and non-responder patient groups are analysed (preferably statistically analysed as distributions) to find a threshold level which differentiates between responder transport activity values and non-responder transport activity values.

Preferably the one or more substrates is a substrate of both MDR1 and MRP1 and if transport activity of any of MDR1 and MRP1 is measured separately the other multidrug transporter is inhibited. In a highly preferred embodiment the substrate is a calcein ester, preferably calcein AM.

In a highly preferred embodiment the activity is quantified as a multidrug activity factor (MAF).

Preferably at least the MDR1 activity is measured. In a particular embodiment at least the MRP1 activity is measured. Preferably at least a composite MDR1-MRP1 activity is measured, preferably with a substrate of both MDR1 and MRP1.

Preferably the patient needs switch or modification of the sDMARD therapy.

In a preferred embodiment a transporter activity value is obtained by measuring transport activity of one or more multidrug transporters comprising at least MDR1, and optionally also MRP1, in the CD3$^+$ T-lymphocytes of said sDMARD (preferably csDMARD) treated RA patient before a bDMARD therapy or in an initial phase thereof, by using an MDR1 substrate which is optionally also the substrate of MRP1, Preferably the MDR1 transporter substrate is also a substrate for MRP1. In this embodiment if MDR1 transporter activity is measured or quantified separately MRP1 is inhibited. If the transporter activity comprises activities of both MDR1 and MRP1, the two transporters are not differentiated by inhibition and a composite activity value is obtained.

In a highly preferred embodiment the substrate is a calcein ester, preferably calcein AM.

In a highly preferred embodiment the activity is quantified as a multidrug activity factor (MAF).

In the present invention preferably a bDMARD therapy involves both boDMARD and bsDMARD therapy.

In a highly preferred embodiment the kit measures the drug transport activity of at least two subfamilies of multidrug resistance proteins: MDR1 and MRP1, utilizes calcein-AM, a substrate for targeted extrusion by multi-drug transporters, and the degree of fluorescence is observed.

In an embodiment the kit also comprises MDR1 and/or MRP1 inhibitors, preferably selected from the group consisting of, verapamil, oligomycin, or cyclosporine, preferably verapamil and indomethacin are present.

Definitions

A "detectable fluorescent compound" as used herein is a compound which can be detected by irradiating with an UV or VIS electromagnetic radiation ("irradiating light") and the compound absorbs the irradiating light and emits light (emitted light) at another, preferably longer wavelength than that of the irradiating light. Preferably the "detectable fluorescent compound" is capable of fluorescence i.e. emission of light inside of i.e. within a cell.

The "derivative of a detectable fluorescent compound" relates to a chemical compound that is derived from said detectable fluorescent compound by an actual (not only theoretical) chemical reaction, preferably an actually performed chemical reaction, and from which the original detectable non-fluorescent compound can be regained by a chemical reaction. Preferably the derivative is fluorescent. Preferably derivative has one or more, preferably more, preferably all of the following features: the derivative is substrate to a MDR protein, is hydrophobic, is permeable to cell membranes and can enter a cell by diffusion through the membrane.

"Ester derivative" of a detectable fluorescent compound relates to a derivative wherein upon the chemical reaction an ester is formed wherein preferably the detectable fluorescent compound can be formed again by ester hydrolyses, preferably by intracellular esterases. Preferably the ester derivative is fluorescent. Preferably the ester derivative is substrate to a MDR protein.

Preferably inside the cell the derivative compound is cleaved by intracellular enzymes, in case of ester derivatives by esterase activity, resulting in a fluorescent non-membrane permeable form of the derivative, which is preferably hydrophilic or charged, and which is preferably not a substrate of the transporter protein.

A "calcein derivative compound", as used herein, refers to a derivative of calcein (CAS No. 1461-15-0, alternative name: fluorexon) with the properties, e.g., of being a substrate to a MDR protein; being permeable to cell membranes, so as to diffuse through the extracellular membrane and enter a cell; and having low sensitivity to $Ca^{2+}$ ions, $Mg^{2+}$ ions, and pH.

For example, in case of the non-fluorescent acetomethoxy derivate of calcein (calcein AM, AM=acetoxymethyl) after it is passively diffused into the cells, intracellular esterases remove the acetomethoxy group, the molecule gets trapped inside as calcein is not a substrate of MDR1 and MRP1, and gives out strong green fluorescence.

Calcein derivatives compounds include, but are not limited to, acetoxymethyl esters of calcein, e.g., calcein-AM, calcein blue AM, or carboxycalcein blue AM, or an acetate ester of calcein [see, e.g., Haugland, Richard P. Handbook of fluorescent probes and research products. Molecular Probes, Inc; 9th edition (2002)].

"Measuring" or "measurement" is understood herein as quantitative characterization of a physical object or entity or a multitude (population or plurality) thereof, or their function or quantitative characterization of a physical or chemical process, comprising the assignment of a quantity, value, e.g. a numerical value or a number characteristic of the object or entity or multitude or function or process, by comparison with units and, in comparison with other object or entity or multitude or function or process. Preferably a measurement is consistent with methods known in the art or the international guidelines of metrology. The magnitude is the numerical value of the characterization, usually obtained with a suitably chosen measuring instrument, whereas the unit assigns a mathematical weighting factor to the magnitude that is derived as a ratio to the property of an artefact used as standard unit or a natural physical quantity as unit.

"Quantifying" or "quantification" or "quantitation" is understood herein as an assignment of a physical quantity to a physical object or entity or a multitude (population or plurality) thereof, or their function or quantitative characterization of a physical or chemical process, expressed in a numerical value or number and units, and, in comparison with other object or entity. Preferably "quantifying" or "quantification" is a measurement or an essential part of a measurement.

The measurement has an uncertainty which may represent the random and systemic errors of the measurement procedure. The skilled person is aware of this and can handle this error in view of the measurement or quantification applied.

"Comparing" two levels preferably two activity levels are understood herein to include a comparison of quantities expressed in numerical values characterizing said levels to establish which is higher or lower, or establishing a difference or establishing a ratio of the levels, or values derived from the levels, optionally completed with other mathematical procedures as the quantification or calculation method requires.

A "membrane transporter" is a membrane integrated protein, which is permanently anchored in the membrane having a membrane spanning part and having parts on both sides of the membrane, wherein it is capable of transporting, e.g. exporting or extruding or importing entities, either actively or passively through the membrane into which it is integrated in. The entity can be e.g. a molecule or a molecule ion which is preferably fluorescent.

"ABC transporter" stands for ATP-binding cassette transporters which are a superfamily of membrane transporters that utilize the energy of adenosine triphosphate (ATP) hydrolysis to carry out certain biological processes including transport of entities across membranes. Denominations and subfamilies of ABC transporters are used herein as assigned by the HUGO Gene Nomenclature Committee (HGNC). For example, membrane transporters of the "ABCG family" belong to the G subfamily of ABC transporters consisting of half-transporters, which oligomerise to form the functional transporter.

A "multidrug transporter" is an ABC transporter, also mentioned herein as an ABC multidrug transporter, which can transport from the cell, in the membrane of which it is present, a multiplicity or preferably a wide variety of chemical compounds.

"Multidrug resistance", as used herein, refers to the ability of cells to develop resistance to a broad range of structurally or functionally unrelated drugs by multidrug transporter(s). Preferably, "multi-drug resistance" refers to the state which is dependent on expression or overexpression of MDR1, MRP1, or a related homologue, and/or on amplification of a gene encoding said multi-drug transporter protein.

"ABC transporter activity", i.e. the "activity" of an ABC transporter protein refers to any activity exerted by the said transporter protein including e.g. its biological function, "transport activity", i.e. transport of a drug through the membrane carrying the said protein, or ATP-ase activity, as far as it is an indicator of transport activity, like substrate stimulated ATP-ase activity. Preferably the activity measured in the present invention characterized or is related to or correlates to transport activity of the multidrug transporter.

A "substrate" of an ABC transporter protein is a compound that can be transporter from the cell through an ABC transporter mediated active transport mechanism.

In a preferred embodiment the ABC multidrug transporters the activity of which is measured in the present invention are selected from the following transporters:
ABCB1 (MDR1) which belongs to the "ABCB family" belong to the B subfamily of ABC transporters;
ABCC1 (MRP1) which belongs to Multidrug Resistance Proteins (MRPs) of the "ABCC family" of the C subfamily of ABC transporters;
and in a preferred embodiment ABCG2 (other names among others: BRCP, MXR1, CDw338) which belong to membrane transporters of the "ABCG family" i.e. of the G subfamily of ABC transporters consisting of half-transporters, which oligomerise to form the functional transporter.

By "measuring transport activity" of a multidrug transporter it is understood that in cells or in a population of cells in which the given multidrug transporter resides or assumably resides the transport activity is measured and/or quantified wherein preferably the activity is total or overall transport activity of one or more multidrug transporter(s). In a preferred embodiment if the expression of the transporters is increased the activity also increases.

In general, any physical quantity which quantitatively characterizes the transport activity of the multidrug transporter can be applied in the present invention. In a preferred embodiment the physical quantity is obtained by comparison of a value obtained for cells in which the multidrug transporter is active with a value obtained for cells in which it is inhibited.

In a preferred embodiment the activity is measured via or with a substrate compound which is able to get through the cell membrane and to be transported from the cell in which the transporter resides.

In a particular preferred embodiment the activity is measured via or with a substrate compound which is a "derivative of a detectable fluorescent compound" and is able to get through the cell membrane and to be transported from the cell in which the transporter resides, wherein within the cell the derivative is converted to the detectable fluorescent compound which is non-membrane permeable, which is preferably hydrophilic or charged, and which is preferably not a substrate of the transporter protein. Preferably the derivative is an ester derivative. Highly preferably the derivative is a "calcein derivative compound". Preferably the detectable fluorescent compound is detected within the cell.

Upon measuring or quantifying (or any equivalent expression) transport activity in a preferred embodiment the activity is quantitatively characterized by a factor which comprises or is related or is proportional to the difference between the fluorescence of the detectable fluorescent compound in the cells measured in the presence of an inhibitor of the one or more membrane transporter and the fluorescence measured in absence of said inhibitor i.e. when the transporter is active. This difference is higher if the transporter is active because the fluorescence provide by the compound in the cell in lack of the inhibitor is lower as the compound (or in case its derivative is applied the derivative) is transported.

By "measuring calcein compound" is meant determining the amount of the calcein compound which accumulates in a cell as an inverse indication of the amount of calcein derivative extruded from the cell by a multi-drug transporter protein.

Techniques for measuring intracellular calcein include, but are not limited to, flow cytometry, fluorimetry, or cell imaging. Use of calcein as a fluorescent probe, in combination with these techniques, provides a quantitative, functional assay of activity of certain multidrug transporter, e.g. of MDR1 and MRP1 activity. By "exposing" is meant placing the calcein compound in the environment of the cells of the biological specimen, e.g., by adding the calcein compound to the media in which the cells of the biological specimen are incubated, so as to allow the calcein compound to enter the cells.

In a preferred embodiment the transport activity of the MDR transporter is measured via the transport (extrusion) of the derivative compound as the difference between the amount of the dye accumulated in the presence and absence of inhibitors. The fluorescence measurement in the presence of an inhibitor constitutes the maximal (potential) fluorescence ($F_{max}$) with the given cell population when the multidrug transporters are rendered non-functional. The fluorescence measurement in the absence of an inhibitor constitutes the minimal fluorescence ($F_0$) with the given cell population when the multidrug transporters are functional. This represents a standardization method, which eliminates unknown cell type-specific variables that influence cellular calcein accumulation, such as esterase activity, cell size, etc.

In a preferred embodiment quantitation or quantifying of this fluorescence is carried out through the development of the MDR Activity Factor (MAF) which is calculated as the ratio of the said difference ($F_{max}-F_0$) and of the maximal fluorescence, i.e.

$$MAF = (F_{max} - F_0)/F_{max}$$

or if expressed in percentage, $MAF = 100 \times (F_{max} - F_o)/F_{max}$.

MAF in percentage is often given as MAF %, however, in the present description this is not indicated, however, the MAF values given herein are given in percentage unless otherwise indicated.

The transport activity of MDR1 and MRP1 can be easily distinguished with selective inhibitors. Optionally other membrane transporters can be inhibited.

By "kit" is meant a package, collection, or container of materials intended to aid one in use of the assay of the invention. By "instructions" is meant a list of steps, or a description of the invention, intended to instruct a practitioner, e.g., a laboratory clinician or technician, to conduct an assay of the invention. The instructions can be written, oral (e.g., on an audio tape medium), or visual (e.g., on a video tape medium).

By a "biological sample", is meant a sample comprising living immune cells obtained from a mammal and optionally processed. The biological sample can be isolated from the mammal as a body fluid, preferably blood or synovial fluid. Preferably the biological sample is a blood sample. Preferred immune cells are at least T-lymphocytes and/or T lymphocyte subsets and optionally or additionally B-cells.

A "patient" is a subject, i.e. a is an individual of a human or a mammalian species who is or intended to be under medical or veterinarian observation, supervision, diagnosis or treatment of a condition.

Preferably the individual is a primate, a hominid or a human.

A "treatment" refers to any process, action, application, therapy, or the like, wherein the subject or patient is under aid, in particular, medical, or veterinarian aid with the object of improving the subject's or patient's condition, either directly or indirectly.

A "therapy" is understood herein as a method for treatment in which a given medicament or pharmaceutical composition is administered to said patient, preferably administered for a certain period of time with the object of improving the subject's or patient's condition.

A "sDMARD" is a "synthetic disease-modifying antirheumatic drug", which is a synthetic chemical compound defined by their use in rheumatoid arthritis to slow down disease progression by targeting the immune system or any immune system pathway and by a mechanism other than lowering inflammation specifically. csDMARD are different from NSAID (non-steroidal anti-inflammatory drugs).

A "csDMARD" is a "classic synthetic" or "conventional synthetic disease-modifying antirheumatic drug", preferably with a broad spectrum, which is a synthetic chemical compound defined by their use in rheumatoid arthritis to slow down disease progression by targeting the immune system, typically broadly or in a way not specified yet, and which has been developed not specifically to target JAK inhibition or a specific pathway inside immune cells. Thus, csDMARD are a subgroup of sDMARDs (Smolen, Landewe et al. 2017).

In a preferred embodiment the csDMARD is selected from the group of compounds consisting of azathioprine, cyclophosphamide (also used in lupus in patients who do not respond to traditional therapy or who experience kidney damage), cyclosporine (used sometimes for lupus in people who do not respond to other therapies), hydroxychloroquine sulfate (an antimalarial drug), leflunomide (people who cannot tolerate methotrexate may take leflunomide. It can also be taken in combination with methotrexate), methotrexate, mycophenolate mofetil (may be used in people whose RA does not respond to other therapies), sulfasalazine (may be used in a triple therapy combination for RA (methotrexate, sulfasalazine, hydroxychloroquine), preferably selected from methotrexate, chloroquine and salazopryne and optionally glucocorticoids.

In a preferred embodiment the definition of "csDMARD" does not involve glucocorticoids.

A "tsDMARD" is a "targeted synthetic disease-modifying antirheumatic drug", which is a synthetic chemical compound which has been developed to specifically target the JAK kinase pathway In a preferred embodiment the tsDMARD is selected from the group consisting of baricitinib, apremilast (Otezla) and tofacitinib (Xeljanz).

A "bDMARD" is a "biological synthetic disease-modifying antirheumatic drug", which is a biological molecule produced by living cells and which has been developed to block an important mediator participating in the development or in the maintenance of chronic inflammation. The term bDMARDs involve biological originator (bo) and biosimilar (bs) DMARDs. A boDMARD and its corresponding bsDMARD are, nevertheless, expectably equivalent from the point of view of the present invention. Based on their targets, bDMARDS include:

tumour necrosis factor (TNF)-inhibitors (adalimumab, certolizumab pegol, etanercept, golimumab, infliximab as boDMARD and their biosimilars), costimulation inhibitor (abatacept);

IL-6 receptor blocker (tocilizumab, sarilumab)

IL-6 inhibitors (clazakizumab, sirukumab)

anti-B cell agent (rituximab)

"Switch" of a therapy means an alteration of the therapy which comprises the application of a medicament or pharmaceutical composition which has not been applied previously. In an embodiment it involves the parallel abandonment of the medicament or pharmaceutical composition administered previously to said patient. In another embodiment it involves the continued administration of the medicament or pharmaceutical composition administered previously to said patient, either in a modified or in an unmodified doses or regime.

Preferably the condition is rheumatoid arthritis.

In particular, a "switch of the therapy" or an "alteration of the therapy", as used herein, relates to an initial DMARD therapy of rheumatoid arthritis, and comprises a modification of sDMARD therapy either to a combination of the same sDMARD (or a combination of sDMARDs) and a bDMARD, or to a combination of a different sDMARD or a different combination of sDMARDs and a bDMARD;

a modification of sDMARD therapy to a therapy with a bDMARD alone, or another sDMARD, in particular a tsDMARD;

wherein preferably the initial DMARD therapy is an csDMARD therapy.

Highly preferably the initial csDMARD therapy is methotrexate therapy.

"Assessing" the success or outcome of a treatment or therapy is understood herein as a method, e.g. a diagnostic type method resulting in a quantitative value which predicts whether a given treatment or therapy will be effective to a given patient and thereby may contribute to a decision on the way of treatment or therapy in the future or on the continuation or alteration of it. Assessing normally involves measurement including calculation and preferably involves consideration of the results and/or drawing conclusion.

As used herein the singular forms "a", "an" and if context allows "the" include plural forms as well unless the context dictates otherwise.

The term "comprises" or "comprising" or "including" are to be construed here as having a non-exhaustive meaning and allow the addition or involvement of further features or method steps or components to anything which comprises the listed features or method steps or components.

The expression "consisting essentially of" or "comprising substantially" is to be understood as consisting of mandatory features or method steps or components listed in a list e.g. in a claim whereas allowing to contain additionally other features or method steps or components which do not materially affect the essential characteristics of the use, method, composition or other subject matter. It is to be understood that "comprises" or "comprising" or "including" can be replaced herein by "consisting essentially of" or "comprising substantially" if so required without addition of new matter.

BRIEF DESCRIPTION OF THE FIGURES

FIG. 1. DAS28 values at different sampling time points in Responder (A) and Non-responder (B) RA patients. *$p < 0.05$ vs. 0 wk. DAS28 is a scoring system to determine activity of RA based on clinical symptoms and quality of life of patients. While an improvement can be observed with decreasing scores in Responders during bDMARD treatment, this improvement is not present in Non-responders.

FIG. 2. Activity of the investigated transporters on CD3$^+$ cells in controls as well as before (A.1-4) and at 6 weeks after (B.1-4) the start of bDMARD therapy in RA patients. *p<0.05 vs. Responder.

FIG. 3. ROC analysis was performed to evaluate the predictive value of MAF for response to treatment in RA patients at the start of biological therapy and at 6 wk. Patients with MAF values above the respective cut-off thresholds are likely to be Non-responders to treatment. (A) $MAF_C$ of CD3$^+$ cells at 6 wk: p=0.033, AUC=0.72; (B) $MAF_C$ of CD3$^+$ cells at 0 wk: p=0.043, AUC=0.68; (C) $MAF_{MDR1}$ on CD3$^+$ T cells at 6 wk: p=0.049, AUC=0.69; (D) $MAF_{MDR1}$ on CD3$^+$ cells at 6 wk: p=0.048, AUC=0.70.

FIG. 4. ROC analysis was also performed to determine the predictive value of $MAF_{MDR1}$ at the time of diagnosis (0 week); in comparison with $MAF_C$ of CD3$^+$ cells at 0 wk (A). When $MAF_{MDR1}$ of CD3$^+$ T lymphocytes is above 17.4 (B), RA patients are likely to be non-responder to bDMARD treatment. Although statistical significance is not present (p=0.24) the sensitivity (58.3%) and the specificity (81.5%) are high enough to use this value as a treatment prediction marker.

The curves demonstrate cut-off values based on various sensitivity and specificity values. The closer we are to the upper left corner of the graph, the more specific and sensitive the cut-off value is. Since no test with perfect specificity and sensitivity exists in real life, a compromise needs to be made against variable specificity and sensitivity values. In our calculations, these values were chosen to be above 60-70% where possible.

DETAILED DESCRIPTION

Current Treatment Recommendations in RA

RA is a common inflammatory rheumatic disease which causes persistent pain, stiffness and joint damage resulting in significant disability, loss of quality of life and employment. The disease mostly affects women and it appears at the 5$^{th}$ decade of the life.

Based on current guidelines, treatment aims to induce clinical and radiological remission for optimizing physical function, improving the quality of life and work capacity and reducing the risk of comorbidities (Linde, Sorensen et al. 2010; Provan, Semb et al. 2011; van der Heijde 2012; Kavanaugh, Fleischmann et al. 2013; Thiele, Huscher et al. 2013; Radner, Smolen et al. 2014). Current treatment guidelines recommend treatment with csDMARD, in particular, MTX eventually in combination with glucocorticoids to be administered for newly diagnosed RA patients which is applicable in several cases. If the first line MTX therapy does not improve symptoms the next step may be either to switch to another csDMARD (e.g., sulfasalazine, leflunomide, hydroxychloroquine) or to add a biological DMARD (bDMARD) to csDMARD e.g. MTX therapy.

The activity of RA in patients is characterized or quantified by a combined index called Disease Activity Score (DAS28) (Fransen and van Riel 2005). It has been extensively validated for its use in clinical trials in combination with the European League Against Rheumatism (EULAR) response criteria. The DAS28 score is based on the examination of 28 joints.

There are a wide range of measures of disease activity in RA including: examination of the joints for swelling and tenderness, applying a global score of pain and overall status, possibly in the form of questionnaires, measuring blood markers of inflammation (e.g. ESR and CRP), the presence of anti-citrullinated antibodies (ACPA) measurement by X-rays or other, possibly newer imaging techniques such as ultrasound and MRI, however, an RA specific biomarker to determine prognosis and/or treatment response has not characterized yet.

Evaluation of response to a treatment can be made much easier and more objective using the DAS or DAS28. The DAS will provide a number between 0 and 10, indicating how active the RA is at this moment, however, DAS28 serves as a real-time data, it does not reflect to the possible disease outcome.

MDR protein function may also predict patient response to csDMARD treatment as well as biological treatment helping the physician to tailor the therapy. However, switching to biologicals (bDMARDs), including the case when csDMARD treatment is continued in parallel, is often challenging due to unpredictable drug susceptibility and high costs, especially in patients with mildly elevated DAS28 scores.

Earlier results of the present inventors and others by measuring MDR1, MRP1 and BCRP activities with the SOLVO MDQ Kit™, with cell surface staining applied to differentiate CD3$^+$, CD4$^+$ and CD19$^+$ cells suggested that low BCRP and MRP1 MAF activities on CD3$^+$ cells may predict the need to start biological therapy in RA patients whose symptoms do not improve on csDMARD treatment. In this setting DAS28 scores, CRP, IL-6, aCCP and RF values were also recorded. It has been suggested that further decrease of CD3$^+$ BCRP and increase in CD3$^+$ MRP1 MAF upon follow-up may indicate a good therapeutic response to biological therapy.

To date, although the role of MDR transporter activity in the prediction of response to MTX has been characterized to some extent in RA (see the Background Art chapter above), little is known about the relation of MDR proteins to therapeutic success of biologicals. In contrast to MTX and other csDMARDs, these molecules do not enter the cell, and are therefore not substrates of MDR proteins. However, the cytokines they target are known to interact with these transporters which may provide an indirect effect on these transporter, hitherto largely unknown.

In the prior art clear guidance was not provided as to how to predict the effectiveness of a bDMARD therapy, in particular, anti-TNF therapy, after a csDMARD therapy has been found insufficient before biological therapy is started, in particular not by measuring multidrug transporter activity.

The present inventors have unexpectedly recognized that measuring at least MDR1 or MRP1 activity or MDR1 and MRP1 composite ($MAF_C$) activity in CD3$^+$ cells in early stage of bDMARD treatment or even before bDMARD treatment a prediction can be made on the effectiveness of bDMARD therapy. Further measurements may also help further the reliability as disclosed herein.

The results of the present inventors indicate that the determination of $MAF_C$ values in CD3$^+$ cells of RA patients is of predictive value prior to the initiation of biological therapy to establish whether the patient will demonstrate sufficient therapeutic response to a biological therapy, in particular anti-TNF therapy or anti-T-cell therapy. Moreover, it has been found that determination of $MAF_{MDR1}$ values in CD3$^+$ cells of RA patients is also appropriate to find a threshold which is predictive prior to the initiation of biological therapy to decide whether the patient will be respondent or non-respondent to biological therapy. demonstrate sufficient therapeutic response. A similar tendency could be observed with MRP1 at 0 weeks of the bDMARD treatment, however, in the experiments the distributions of the $MAF_{MDR1}$ values for responders and non-responders could be separated to a lesser extent. Nevertheless, a threshold value can plausibly be found in this type of measurement as well which may predict non-responders e.g. with a sufficient sensitivity or at least positive predictive value.

It is of particular advantage of both $MAF_{MDR1}$ and $MAF_C$ values are determined and both of them is above the given pre-determined threshold whereby the patient can be considered as a non-responder, or not higher than the threshold wherein the patient is an expectable responder to the bDMARD treatment. Additionally, determining $MAF_{MDR1}$ values will contribute to the reliability of the test.

It is of high importance that the present method is appropriate to provide predictors before the start of the bDMARD therapy as in this way applying an expensive therapy, with special danger of side-effects and loss of time by using an ineffective therapy. The results provide an option to decide about further treatment before symptoms reflect the success of the therapy. As in RA the window of opportunity to apply therapy is limited, the invention is useful to find the appropriate treatment in time.

Nevertheless, the method can also be applied in an initial state of the bDMARD therapy for example within the first two months the latest or preferably earlier, e.g. in the first 6 weeks or the first 4 weeks or the first 2 weeks of the therapy. Certain predictive values can even be more pronounced in this stages.

Thus, if bDMARD therapy has already been started, it makes sense to run the method of the invention as early as possible. Moreover, if the first measurement resulted in a result which allowed to try and initiate bDMARD therapy it is or may be advisable to repeat the measurement at a later though still relatively early stage, e.g. at 4 to 7 weeks of the bDMARD therapy. Measuring $MAF_C$, $MAF_{MRP}$ and $MAF_{MDR}$ values in $CD3^+$ cells at 4 to 7 weeks after the start of biological treatment further improves the accuracy of prediction as to whether adequate therapeutic response may be expected. This knowledge provides help the physician to individually tailor the patient's therapy in a timely manner resulting in positive implications with regards to the cost of treatment and the spectrum of side effects.

The skilled person will understand that MAF values report on transport activity of the substrate applied, and other methods to measure or quantify transport activities in the $CD3^+$ T-lymphocytes can be used in the present invention. Also using a substrate which is transportable by both MRP1 and MDR1 is preferred as when a composite activity value is to be obtained this can be done simply and reliably in a single measurement. The individual activity values for MDR1 and MRP1 can be obtained by using specific inhibitors in this setting.

It is of particular advantage is the substrate is reportable, preferably fluorescent and the results can be obtained and quantified by flow cytometry. This is particularly advantageous as in the present setting the transport activity is to be measured in $CD3^+$ T-lymphocytes only.

The skilled person will also understand that applying the MAF values to report on activities is preferred as this way of quantification of the results reliably reports the activity in a manner which is highly independent from conditions of the measurement, like flow cytometry parameters, and rather sensitive to the cell type which is in line with the nature of this inventive method.

In the present invention when patient samples are measured and responsiveness is assessed no control samples are necessary as pre-determined threshold (cut-off) values are applied.

The Utility of csDMARDs and bDMARDs in RA

Today, recommendations for RA treatment are based on the current EULAR guideline (Smolen, Landewe et al. 2017). The most important feature of this guideline is that the decision making should be shared between the patient and the rheumatologist, however, the aim of the therapy is to achieve the treatment goal of remission or at least low disease activity within the time frame of 6 months, at least 50% clinical improvement within 3 months is desirable (Aletaha, Alasti et al. 2016). To achieve this goal Therapy should be started as soon as possible, preferably at the time of diagnosis. Importantly, therapy success should be monitored regularly especially in active disease (every 1-3 moths) and, if there is no improvement, or the goal is not reached by 6 moths, therapy should be modified. If the therapy goals are achieved, the dose of the respective medicine could be declined, or, in complete remission, terminated.

For checking treatment success, the determination of DAS28 levels together with the measurement of rheuma factor (RF), CRP, ACPA and erythrocyte sedimentation rate (ESR) are widely used and a person skilled in the art is able to apply these methods to the present invention.

csDMARDs, especially MTX together with lefluonomide, sulfasalazine and hydroxychloroquine, or in some cases, glucocorticoids, serve as Phase I therapy. Although these agents sometimes have poorly tolerated side effects, MTX should be the first medication in present EULAR recommendations. Importantly, when MTX is contraindicated, or its side effects are poorly tolerated, the patient should be switched to leflunomide, or bDMARD.

Anti-TNF agents (infliximab, trade name: Remicade; etanercept, trade name: Embrel, adalimumab, trade name Humira, golimumab, trade name: Simponi and certolizumab pegol, trade name: Cimzia) serve as the first-line biological originator (bo)DMARDs, since biosimilar (bs)DMARDs are also available. The first suggested anti-TNF agent is infliximab (IFX), however, it is a chimeric monoclonal, thus, anti-drug antibodies may develop which drastically cuts down the efficiency of this expensive therapy. When first-line anti-TNF agent (bo or bs, respectively) is not successful, another anti-TNF antibody should be used. Importantly, drugs altering immune response should carefully be applied, as in some cases, it may lead infections, moreover, to cancer development (Bongartz, Sutton et al. 2006). Importantly, these Phase II therapies should be given in parallel with csDMARDs or glucocorticoids to make therapy more effective (Nurmohamed and Dijkmans 2008).

When the treatment goal was not reached by using anti-TNF agents, other bDMARDs should be used. These drugs are targeting costimulation (T cell activation, abatacept, trade name: Orencia), causing B cell depletion (rituximab, trade name: Rituxan), blocking IL-6 receptor (tocilizumab, trade name: Actemra, sarilumab, trade name: Kevzara), IL-6 inhibitors (clazakizumab, sirukumab), or blocking IL-1 receptor (anakinra, trade name: Kineret). These treatments, together with tsDMARDS serve as Phase III therapy. tsDMARDs are inhibiting JAK kinases (tofacitinib, trade name: Xeljanz, or baricitinib, trade name: Olumiant). Importantly, Phase II and Phase III therapies should be given in parallel with csDMARDs and it is based on the patient's necessities.

It is then up to the medical personnel guiding the treatment that in case of non-responsiveness for a patient treated or to be treated by anti-TNF therapy or anti T cell activation therapy should be switched to a tsDMARD therapy or at first other bDMARD therapy of different target, like B-cell depletion or IL-6 inhibitors or blocking IL-6 receptor or IL-1 receptor should be applied. Advisably the contemporary EULAR guidance or its national variant should be observed.

MDRs in Health and Disease

Transport of compounds between the intra- and extracellular compartments is an essential physiologic phenomenon. For this, several transmembrane pumps evolved, showing strong sequence homology between different species.

The core functional unit of ABC transporters contains two membrane-spanning domains, each of which typically contains 6 transmembrane (TM) helicases. In the intracellular compartment, 2 nucleotide-binding domains (NBDs) are localized which contain Walker A and Walker B domains, that are necessary for ATP binding and hydrolysis (Deeley, Westlake et al. 2006; Silva, Almeida et al. 2015), As ABC transporters originally involved in the detoxification of the organism, the members of the ABC transporter family are expressed on a wide variety of tissues and organs, like intestine, lung, liver, testes, placenta, skeletal and cardiac muscle and on the endothelial surface of the blood-brain barrier (Flens, Zaman et al. 1996; St-Pierre, Serrano et al. 2000; Wijnholds, deLange et al. 2000; Mercier, Masseguin et al. 2004; Castilho-Martins, Canuto et al. 2015). The majority of ABC transporters are expressed on the apical and basolateral surface of polarized cells (Hipfner, Gauldie et al. 1994; Evers, Zaman et al. 1996), however, in special cases, i.e. in drug selected cell lines, MDR1 is shown to be localized in the Golgi complex as well (Cole, Bhardwaj et al. 1992).

Beside their crucial role in the maintenance of homeostasis, ABC transporters are also involved in the phenomenon, called multidrug resistance (MDR), which makes therapy ineffective by removing drugs from target cells. Since MDR is the principal mechanism by which many tumours develop resistance to chemotherapeutics or immunosuppressant drugs administered in different types of leukaemia, solid tumours and autoimmune diseases and to patients who underwent transplantation. Conventional anticancer drugs (doxorubicin, gefitinib, irinotecan, methotrexate, paclitaxel, tamoxiphen, topotecan, etc.) are substrates of MDR transporters. Moreover, MDR transporters play distinct role in the fine tuning of the immune response.

qRT-PCR, immunohistochemistry and Western blots are the most frequently used methods to determine the MDR transporter status in clinical samples. More recently, mass spectrometry based methods have been described to quantify transporter expression (Prasad, Lai et al. 2013). On the other hand, several polymorphisms affecting transporter functions have been reported (Porcelli, Lemos et al. 2009; Lee, Chau et al. 2010). Therefore, relevance of even protein levels as solitary pieces of data is questionable. Some of the genetic variants affect transporter trafficking, and, thus, FACS-based determination of cell surface expression of MDR transporters is a significant progress (Damiani, Tiribelli et al. 2006). However, antibodies recognizing the extracellular MDR1 (Georges, Tsuruo et al. 1993; Vasudevan, Tsuruo et al. 1998) and BCRP (Telbisz, Hegedus et al. 2012) epitopes are conformation sensitive, making their determination challenging.

Such methods can be applied in and to the present invention, however, adaptation is needed. Using fluorescent substrates and flow cytometry and quantifying the results as MAF values as shown herein is advantageous due to reliability and simplicity. Using a calcein ester which is substrate of both MDR1 and MRP1 and which is trapped in the CD3$^+$ T-lymphocytes once cleaved are of particular advantage as explained more specifically below.

The Determination of Transporter Activities

The transporter activity can be among other measured by a kit designed for functional quantitative measurement of drug resistance in live cells. The procedure is preferably fast, sensitive, and quantitative. The procedure should preferably measure the drug transport activity of at least two subfamilies of multidrug resistance proteins: MDR1 and MRP1. MDR1 and MRP1 are ATP-dependent trans-membrane proteins that remove hydrophobic xenobiotic compounds (typically environmental toxins) from the cell. A preferred kit utilizes calcein-AM, a non-fluorescent hydrophobic compound that enters all cells by passive diffusion via the plasmamembrane. Calcein-AM is an excellent substrate for targeted extrusion by multi-drug transporters. If MDR1 and MRP1 are active, the hydrophobic calcein-AM will be removed intact before it can be hydrolyzed. If MDR1 and MRP1 are not active, enzymatic cleavage of the calcein-AM by endogenous esterases results in the fluorescent hydrophilic free-acid, calcein, which is retained within the cytoplasm. Normal, drug sensitive cells will fluoresce when exposed to calcein-AM. The degree of fluorescence observed in test cells is inversely proportional to MDR1 and MRP1 activity. An example for such a kit is The SOLVO MDQ Kit which has CE-IVD certification (available from MDQuest, Szeged, Hungary).

Quantitation of this fluorescence is possible through the development of the MDR Activity Factor (MAF). The dye efflux activity of the MDR transporter is measured as the difference between the amount of the dye accumulated in the presence and absence of inhibitors.

The fluorescence measurement in the presence of an inhibitor specific to both MDR1 and MRP1 constitutes the maximal potential fluorescence with the given cell population when the multidrug transporters are rendered nonfunctional. This represents a standardization method, which eliminates unknown cell type-specific variables that influence cellular calcein accumulation, such as esterase activity, cell size, etc. This, in turn, allows for intra- and interlaboratory comparison of test results and MAF values. The transport activity of MDR1 and MRP1 can be easily distinguished with inhibitors specific to one of these proteins.

Inhibitors, which are known to those skilled in the art, preferably includeverapamil, and also included, but are not limited to, e.g., verapamil, indomethacin, oligomycin, or cyclosporin.

The kit has been optimized for and its preferred use is in flow cytometry, but can be adapted for use in other cell-based assay formats such as fluorescence microscopy, spectrophotometry, or 96 well plate assays. If these applications are utilized it is necessary to consider the following:

Heterogeneous cell populations accumulate calcein at different rates, which cannot be resolved by fluorometry (cuvette or plate reader).

Homogeneous cell population can be easily tested in the above-mentioned formats.

For consistency and reproducibility, adequate mixing of cell suspensions and temperature control are necessary.

Protocol adaptation for other formats will be necessary.

A more detailed description of a particular kit is provided in the Examples.

Practical Aspects in Carrying Out Transport Activity Measurements

In particular, for determining transporter functions in RA patients with commercially available detection kits, application of any internal and external controls are not required, since the cut-off values for each transporters in all time points are clearly defined.

For testing the performance of the preferred kit, cell lines overexpressing of MDR1, MRP1 and BCRP could be used.

For checking the flow cytometry equipment, commercially available fluorescent microbeads are recommended.

In one embodiment of the method of detecting multi-drug resistance in a biological sample, the control cells can be a portion of the biological sample itself, the method further including exposing the control cells to an inhibitor of multi-drug resistance. By using portions of the same biological sample, or by controlling the temporal sequence by which the components are added, the control acts as an internal, or "self", control.

The MAF values of healthy adults on CD3$^+$ T lymphocytes have already been determined according to the CLSI guideline C28-A2. In that study, 120 healthy adults (age between 18 and 74 years) were enrolled. In parallel with measuring MAF values, CD4/CD8 ratio, blood cell count, liver and kidney function were determined. For performing transporter activity measurements, 6 mls of K$_3$EDTA anticoagulated peripheral blood samples were collected from each individual. PBMCs were separated by using Ficoll Histopaque density gradient centrifugation according to the manufacturer's instructions. The applied assay was performed as it was described by the instructions for users. After running assay, CD3$^+$ cells were labelled with PerCP or FITC conjugated anti-CD3 antibodies. The measurements were carried out on a BD FACSCalibur flow cytometer equipped with 488 nm argon and 635 nm red diode lasers. The calculation of MAF values were performed as it was described previously. Importantly, no statistical significance was determined between men (n=62) and women (n=58). Interestingly, the age of the individual had no impact on MAF values in case of MRP1 and BCRP, however, in case of MDR1 and MAF$_C$ values, a negative correlation was determined between the values and the age of the studied individuals. Based on the previous facts, the cut-off values for transporter activities, which can be considered as an average for the healthy European adult population, are the following: MAF$_C$: 16.5; MAF$_{MDR1}$: 12.9; MAF$_{MRP1}$: 2.5; MAF$_{BCRP}$: 3.4.

Finding an Activity Threshold Value to Distinguish Between Responders and Non-Responders.

The receiver operator curve (ROC) is a fundamental tool for diagnostic test evaluation. When the results of a diagnostic test are considered to discriminate between two populations (eg. responders versus non-responders), a perfect separation between the two groups is rarely observed. For every possible cut-off point selected to discriminate between the two populations, there will be some cases with the responder status correctly classified as responder (True Positive), but some responders will be classified into the non-responder group (False Negative). On the other hand, the majority of non-responders will be correctly classified as non-responders (True Negative), but some will be classified as responders (False Positive). In a ROC curve the true positive rate (Sensitivity: calculated as the True Positive/(True Positive+False Negative)) is plotted against the false positive rate (100-Specificity; wherein specificity is calculated as the False Positive/(False Positive+True Negative), i.e. 100-Specificity is the True Negative/(False Positive+True Negative)), demonstrating different cut-off points of a parameter. Each point on the ROC curve represents a sensitivity/specificity pair corresponding to a particular decision threshold. The area under the ROC curve (AUC) is a measure of how well a parameter can distinguish between two diagnostic groups (Zweig and Campbell 1993). While the ROC analysis is widely applied, the skilled person will understand that any means preferably mathematical statistical means for finding a threshold to separate the two overlapping distributions may be applied in the present invention.

Our ROC analysis revealed that the assessment of multidrug activity of peripheral blood lymphocytes carries predictive value for response to bDMARD treatment in RA patients at the start of therapy. Patients with MAF values above the cut-off thresholds are likely to be Non-responders to treatment. Of note, these cut-off values are all below the respective reference ranges in healthy individuals established in our earlier study.

Additional Criteria to Distinguish Between Responders and Non-Responders

MDR-ABC transporters transport a variety of endogenic molecules, such as cytokines and chemokines that play an important role in the pathogenesis of RA and therefore may be used as biomarkers to monitor disease progression in RA. They may also be used as a predictive tool to establish responsiveness to biological therapy. In this multicenter clinical trial, we aimed to assess the predictive value of flow-cytometry based multidrug resistance activity measurement of three clinically relevant MDR proteins (MDR1, MRP1, BCRP) for biological therapeutic response in rheumatoid arthritis in CD3$^+$ and CD19$^+$ lymphocytes before as well as 4 to 6 and 12 weeks after the initiation of biological therapy.

Examples

Methods

Measurement of MDR1 and MRP1 Activities by the Calcein Assay

Quantitative measurement of MDR1 and MRP1 activities in viable cells is carried out using the calcein-assay technology (see U.S. Pat. No. 5,872,014A). As a preferred kit the SOLVO MDQ Kit was used. This method has several advantages against other fluorescent dye accumulation tests: it is quick, quantitative, selective for MDR1 and MRP1 transporters and it has validated internal standard. This assay utilizes the fluorogenic dye calcein-acetoxymethyl ester (calcein-AM) a hydrophobic compound that readily penetrates the cell membrane. After entering into the living cell, the non-fluorescent calcein-AM is rapidly hydrolysed by endogenous esterases to form a highly fluorescent free acid derivative of the dye which becomes trapped in the cytoplasm due to its high hydrophilicity. Another advantage of calcein is the relative insensitivity to changes of various cellular parameters, including intracellular pH, Ca$^{2+}$ and Mg$^{2+}$ concentrations.

As calcein-AM is an excellent substrate of both MDR1 and MRP1, activity of these efflux transporters results in lower cellular accumulation of the fluorescent calcein. Consequently, the more MDR proteins are active in the cell membrane, the less calcein is accumulated intracellularly. In MDR expressing cells, the addition of selective inhibitors of MDR1 and MRP1 blocks the dye exclusion activity of the relevant transporter and increases calcein accumulation in the cells. In the absence of significant MDR transporter activity, the lack of transporter mediated efflux means that the net calcein accumulation is faster in the cells, which, in turn, is not influenced by the presence of an MDR transporter inhibitor or substrate.

Respective activities of MDRs are reflected by the difference between the amount of calcein accumulated in the presence or absence of selective inhibitors. When calculating the MAF values, this accumulation difference is normalized to the dye uptake measured in the presence or the absence of the inhibitor and the results of the assay are expressed in MDR activity factor (MAF) values. Thus, the result of the test is independent from factors influencing the cellular accumulation of Calcein other than the activity of the multidrug transporters. Such factors involve the difference in cellular properties (membrane lipid composition, intracellular esterase activity, cell size, cell surface, etc) and the methodological differences (i.e.: using different equipment, amplification and individual variables). Since the influence of these non-MDR transporter mediated factors are reduced by the normalization approach mentioned above, this facilitate intra- and interlaboratory comparison of MAF values.

Selective inhibitors can be used to distinguish between the transport activity of MDR1 and MRP1. The pan-MDR1/MRP1 inhibitor blocks both MDR1 and MRP1 mediated dye effluxes, providing dye accumulation rate that can be used for standardization, while MRP1 blocker helps to determine MDR1 and MRP1 activity. After a short, simple calculation, separate measurement of multidrug resistance for both MDR1 and MRP1 activity can be obtained.

BCRP activity is measured using a similar principle: intracellular accumulation of the fluorescent BCRP specific probe substrate is measured in the presence or the absence of selective BCRP inhibitor. However, in this case, the BCRP specific probe substrate is direct fluorescent and does not require cleavage by intracellular enzymes.

It is possible to perform MDR activity measurement on a dedicated cell population of interest by labelling them with fluorochrome-conjugated antibodies after running assay procedure. The assay-compatible fluorochromes are listed in Table 1.

TABLE 1

Examples for assay compatible fluorescent conjugates

| Transporter(s) | Dye/substrate | Channel | Compatible fluorochrome |
|---|---|---|---|
| MDR1, MRP1 | calcein | ~515 nm | PerCP; PerCP-5.5 |
| BCRP | mitoxanthrone | ~684 nm | FITC, PE |

Use of the SOLVO MDQ Kit™

The SOLVO MDQ Kit™ was used strictly following the manufacturer's instructions. PBMCs were loaded with fluorescent MDR activity reporter substrates (Calcein-AM for MDR1 and MRP1, em: 515 nm and mitoxantrone for BCRP, em: 684 nm, respectively) and treated with MDR protein specific inhibitors (verapamil for MDR1 and MRP1, indomethacin for MRP1 and KO134 for BCRP, respectively) to obtain multidrug activity factor (MAF) values.

Cell surface staining was applied to select CD3$^+$ T lymphocytes using anti-human CD3-PerCP monoclonal antibodies in case of Calcein-AM stained cells and anti-human CD3-FITC monoclonal antibodies in case of mitoxantrone stained cells according to the manufacturer's instructions.

MAF values were calculated from the difference between the geometric mean fluorescent intensity (MFI) of cells with and without the specific inhibitors, respectively.

$$MAF_C(\text{composite MAF of MRP1 and MDR1}) = 100 \times (F_{max} - F_o)/F_{max}$$

$$MAF_{BCRP}(\text{MAF of MRP1}) = 100 \times (F_{MX} - F_0)/F_{max}$$

$$MAF_{MDR1}(\text{MAF of MDR1}) = MAF_C - MAF_{MRP1}$$

$$MAF_{BCRP}(\text{MAF of BCRP}) = 100 \times (F_{mx} - F_0)/F_{MX}$$

$F_{max}/F_{MX}$: Calcein/mitoxantrone fluorescence with verapamil or KO134, respectively $F_o$: fluorescence without inhibitor $F_{MRP1}$: Calcein fluorescence with indomethacin Patient Recruitment 39 RA patients were recruited at the outpatient clinics of the Department of Rheumatology, University of Debrecen, Hungary and the Department of Rheumatology and Clinical Immunology, Charité, Berlin, Germany. Patients were sampled before the start of biological treatment as well as between 4 and 7 weeks and at 12 weeks of treatment. DAS28 and CRP values were also recorded in parallel with MAF determination. Patients were regarded as non-responders (n=12) if DAS28 values showed a decrease of less than 25% between the start of biologicals and at 12 weeks of treatment. Patient characteristics as well as details of the therapy received are included in Table 2. Healthy controls (n=35) were sampled at the Department of Rheumatology, University of Debrecen, Hungary on a single occasion. They had a negative history of autoimmune disorders including RA and a negative status upon physical examination as well as no infectious symptoms within three weeks before sampling.

Exclusion criteria for all participants included chronic infectious diseases requiring systemic treatment, autoimmune diseases other than RA, immunodeficiencies, allergic diseases and hematological malignancies or solid tumors, age below 18 years. Written informed consent was obtained from all participants and the study adhered to the tenets of the most recent revision of the Declaration of Helsinki.

Peripheral Blood Mononuclear Cell (PBMC) Isolation 6 mls of K$_3$EDTA anticoagulated peripheral blood sample was collected. PBMCs were separated by density gradient centrifugation using Ficoll Histopaque-1077 (Cat. No: H8889, Sigma-Aldrich, St. Louis, Mo., USA) according to the manufacturer's instructions.

Flow Cytometry

Measurements were conducted on a BD FACSCalibur flow cytometer (BD Biosciences, San Diego, Calif., USA) equipped with 488 nm and 635 nm lasers or on a Miltenyi MACSQuant flow cytometer, equipped with 405 nm, 488 nm and 638 nm lasers, respectively.

The SOLVO MDQ Kit was used strictly following the manufacturer's instructions. In this assay, fluorescent reporter substrates are trapped in the cytoplasm and pumped out by MDR proteins depending on the presence or absence of specific inhibitors, allowing for quantitative, standardized assessment. PBMCs were loaded with fluorescent MDR activity reporter substrates (Calcein-AM for MDR1 and MRP1, em: 515 nm and mitoxantrone for BCRP, em: 684 nm, respectively) and treated with MDR protein specific inhibitors (verapamil for MDR1 and MRP1, indomethacin for MRP1 and KO134 for BCRP, respectively) to obtain multidrug activity factor (MAF) values.

Cell surface staining was applied to select CD3$^+$ and CD19$^+$ cells using anti-human CD3-PerCP and CD19-PE monoclonal antibodies (Cat. No: 345766 and 345789, respectively, both BD Biosciences) in case of Calcein-AM stained cells and anti-human CD3-FITC and CD19-PE monoclonal antibodies (Cat. No: 345764 and 345789, respectively, both BD Biosciences) in case of mitoxantrone stained cells according to the manufacturer's instructions. Assay-compatible fluorochromes are listed in Table 1.

Results

ROC analysis was performed to evaluate the predictive value of MAF for response to treatment in RA patients at the start of biological therapy and at 6 wk. Cut-off thresholds were calculated for MAF values with ROCs of adequate p and AUC values (FIG. 3). Patients with MAF values above the respective cut-off thresholds are likely to be Non-responders to treatment ($\text{MAF}_C$ of $\text{CD3}^+$ cells at 0 wk: p=0.043, AUC=0.68; $\text{MAF}_C$ of $\text{CD3}^+$ cells at 6 wk: p=0.033, AUC=0.72; $\text{MAF}_{MDR1}$ on $\text{CD3}^+$ cells at 6 wk: p=0.048, AUC=0.70; $\text{MAF}_{MRP1}$ on $\text{CD3}^+$ cells at 6 wk: p=0.049, AUC=0.69).

In our multicenter clinical trial, 39 RA patients were enrolled. For determining the functional activities of MDR1, MRP1 and BCRP, 6 mls of $\text{K}_3\text{EDTA}$ anticoagulated blood peripheral blood samples were collected. PBMCs were separated by using Ficoll Histopaque density gradient centrifugation according to the manufacturer's instructions. SOLVO MDQ Kit™ assay was performed as it is described in the instructions for users. After performing the assay, $\text{CD3}^+$ T lymphocytes were labelled with PerCP or FITC-conjugated anti-CD3 antibodies for 30 minutes. After removing unbound antibodies, transporter activities were determined on $\text{CD3}^+$ T lymphocytes by flow cytometry.

Clinical characteristics of patients are indicated in Table 2.

TABLE 2

Clinical characteristics of Responder and Non-responder RA patients as well as healthy controls.

| | Healthy controls (n = 35) | Responder (n = 27) | Non-responder (n = 12) |
|---|---|---|---|
| Age (years) | 54 (42-62) | 56 (49-61) | 51 (39-61) |
| Gender (male/female) | 4/31 | 2/25 | 1/11 |
| RA duration (years) | — | 10 (5-14) | 8.5 (5-15) |
| No. of patients receiving MTX | — | 15 (56%) | 6 (50%) |
| No. of patients receiving prednisolone | — | 9 (33%) | 5 (42%) |
| No. of patients receiving adalimumab | — | 2 (7%) | 1 (8%) |
| No. of patients receiving certolizumab pegol | — | 5 (19%) | 3 (25%) |
| No. of patients receiving etanercept | — | 7 (26%) | 3 (25%) |
| No. of patients receiving abatacept | — | 13 (48%) | 5 (42%) |

Data are expressed as median (IQR) for continuous variables and as number (percentage) for categorical variables.
MTX—methotrexate Importantly, in parallel with collecting blood samples at the time of diagnosis (0 week) and during regular checkups (2, 6 and 12 weeks, respectively) DAS28 score was determined and the routinely used inflammatory markers (RF, CRP, ESR, ACPA) were also measured from peripheral blood. bDMARD treatment responsivity was determined on the alterations of DAS28 scores.

Regarding to treatment success (FIG. 1), the baseline DAS28 value was remarkably higher (average: 5.94; 5.11-6.17) as compared with non-responders (average: 4.65; 2.79-4.45). In case of responders, significant DAS28 down regulation was detected 6 weeks after starting bDMARD as compared with 0 week values (3.71 vs 5.94) which became more pronounced at 12 weeks checkup (average: 3.00). In contrary with responders, bDMARD treatment had no impact on DAS28 values neither 6, nor 12 weeks after starting therapy (3.93 and 3.90, respectively).

ROC analysis was performed to evaluate the predictive value of MAF for response to treatment in RA patients at the start of biological therapy and at 6 wk. Cut-off thresholds were calculated for MAF values with ROCs of adequate p and AUC values (FIG. 3, FIG. 4). Patients with MAF values above the respective cut-off thresholds are likely to be Non-responders to treatment ($\text{MAF}_C$ of $\text{CD3}^+$ T lymphocytes at 0 wk: p=0.043, AUC=0.68; cut-off: 21.3; $\text{MAF}_C$ of $\text{CD3}^+$ T lymphocytes at 6 wk: p=0.033, AUC=0.72, cut-off: 12.3; $\text{MAF}_{MDR1}$ on $\text{CD3}^+$ T lymphocytes cells at 6 wk: p=0.048, AUC=0.70, cut-off: 13.9; $\text{MAF}_{MRP1}$ on $\text{CD3}^+$ T lymphocytes at 6 wk: p=0.049, AUC=0.69, cut-off: 6.0). In case of $\text{MAF}_{MDR1}$ of $\text{CD3}^+$ T lymphocytes at 0 wk, the cut-off value is 17.4, however, based on the low patient number, statistical significance was not detected (p=0.24).

MAF values of $\text{CD3}^+$ T lymphocytes from RA patients showed the following values: at the time of diagnosis, $\text{MAF}_C$ values of responders were almost the same as compared with healthy individuals (18.9 vs 18.3), however, in case of non-responders, $\text{MAF}_C$ values on $\text{CD3}^+$ T lymphocytes were significantly upregulated as compared with controls (23.5 vs 18.3). During bDMARD treatment in case of responders, a slight down regulation was detected 6 weeks after starting therapy, however, in later time points, $\text{MAF}_C$ value did not showed any alterations as compared with control samples and values at the time of diagnosis. Importantly, in case of responders, average $\text{MAF}_C$ values were below the cut-off values at the time of diagnosis and 6 weeks after starting bDMARD treatment. In contrary with responders, $\text{MAF}_C$ values of non-responders were significantly higher as compared with healthy controls at the time of diagnosis (23.5 vs 18.3). As same as responders, bDMARD treatment had no impact on $\text{MAF}_C$ values, however, $\text{MAF}_C$ of $\text{CD3}^+$ T lymphocytes during bDMARD treatment were significantly higher as compared with healthy counterparts.

Although in case of $\text{MAF}_{MDR1}$ cut-off value statistical significance was not detected at the time of diagnosis (17.4; 0 weeks), its prognostic value is still high, in particular together with the 6 weeks cut-off value data (13.9). At the time of diagnosis, responder values did not showed any alterations as compared with controls, however, $\text{MAF}_{MDR1}$ values of non-responders were significantly above the control data (19.1 vs 14.6). Prolonged bDMARD treatment had no significant impact on $\text{MAF}_{MDR1}$ values of responders. In case of non-responders, mild down regulation was detected after starting bDMARD treatment as compared with values at the time of diagnosis.

$\text{MAF}_{MRP1}$ values has strong prognostic value 6 weeks after starting bDMARD treatment. At the time of diagnosis (0 weeks?), mild upregulation was detected in RA patients as compared with healthy controls. 6 weeks after starting bDMARD treatment, a mild down regulation was detected as compared with 0 weeks value. Importantly, opposed to responders, a significant upregulation was detected in non-responders (2.2 vs 8.4).

Results are summarized in Table 3.

TABLE 3

Activity of various MDR transporters on CD3$^+$ and CD19$^+$ cells in RA patients and healthy controls.

| | | 0 wk | | 6 wk | | 12 wk | |
|---|---|---|---|---|---|---|---|
| | Control | Responder | Non-responder | Responder | Non-responder | Responder | Non-responder |
| DAS28 | — | 5.94 | 4.65$^b$ | 3.71$^c$ | 3.93 | 3.00$^c$ | 3.90$^b$ |
| | | (5.11-6.17) | (3.33-5.23) | (2.79-4.45) | (3.14-4.50) | (2.23-3.67) | (2.81-4.90) |
| CRP | — | 11.1 | 8.4 | 4.4 | 4.4 | 3.7 | 7.5 |
| | | (2.6-16.6) | (1.4-15.1) | (1.3-7.9) | (1.5-10.4) | (2.1-5.6) | (2.7-11.6) |
| CD3 MAF$_C$ | 18.3 | 18.9 | 23.5$^b$ | 17.1 | 22.7$^b$ | 18.3 | 25.2 |
| | (14.7-22.9) | (14.0-25.2) | (17.1-33.7) | (12.3-22.6) | (16.7-29.2) | (15.7-24.2) | (15.9-30.7) |
| CD3 MAF$_{MRP1}$ | 3.1 | 4.8 | 5.7 | 2.2 | 8.4$^b$ | 5.7 | 7.7$^a$ |
| | (1.2-5.7) | (0.0-8.0) | (2.2-8.0) | (0.0-7.9) | (2.1-11.3) | (3.7-8.5) | (4.0-11.6) |
| CD3 MAF$_{MDR1}$ | 14.6 | 12.9 | 19.1$^b$ | 12.4 | 15.8$^b$ | 12.5 | 13.6 |
| | (12.5-18.1) | (11.0-16.7) | (11.2-24.0) | (11.2-15.4) | (14.3-18.7) | (9.2-17.5) | (6.0-20.0) |
| CD3 MAF$_{BCRP}$ | 2.5 | 3.1 | 5.0 | 2.0 | 3.9 | 1.4 | 4.5 |
| | (0.8-5.7) | (0.0-4.4) | (2.0-8.0) | (0.0-5.5) | (2.5-10.7) | (0.0-4.3) | (1.8-5.8) |
| CD19 MAF$_C$ | 12.8 | 15.1 | 20.6 | 13.2 | 17.6 | 17.4 | 17.6 |
| | (8.9-17.9) | (8.1-22.1) | (13.5-31.0) | (9.3-20.4) | (11.4-27.2) | (13.1-22.3) | (9.2-25.9) |
| CD19 MAF$_{MRP1}$ | 2.2 | 0.9 | 4.4 | 0.6 | 6.8$^b$ | 3.2 | 5.1 |
| | (0.0-6.3) | (0.0-7.7) | (0.0-5.8) | (0.0-5.1) | (0.5-9.6) | (0.3-6.8) | (1.9-10.9) |
| CD19 MAF$_{MDR1}$ | 9.9 | 11.1 | 15.7 | 11.4 | 13.6 | 14.0 | 8.8 |
| | (8.0-14.0) | (6.0-16.3) | (8.4-25.4) | (5.3-14.8) | (8.6-17.7) | (7.1-17.7) | (1.9-15.7) |
| CD19 MAF$_{BCRP}$ | 3.8 | 3.1 | 4.5 | 2.7 | 5.0 | 2.9 | 3.0 |
| | (1.0-6.3) | (0.7-7.0) | (0.0-11.0) | (0.0-5.2) | (3.1-8.4) | (1.3-5.1) | (1.8-3.7) |

Data are expressed as median (IQR),
$p < 0.05$
$^a$vs Control,
$^b$vs Responder,
$^c$vs 0 wk value.
MAF$_C$—composite multidrug activity factor (of MRP1 and MDR1 activity),
MAF$_{MRP1}$—multidrug activity factor of MRP1,
MAF$_{MDR1}$—multidrug activity factor of MDR1,
MAF$_{BCRP}$—multidrug activity factor of BCRP Case Studies Examples from our own clinical trial for predicting patient's response to bDMARD treatment: Patient 1: 53 years old women who received abatacept (T cell blocking agent). Her DAS28 values showed gradient down regulation during the monitored period (5.94; 5.22; 4.11; 3.36, respectively). Her MAF$_C$ and MAF$_{MDR1}$ values at the time of diagnosis were 4.2 and 4.1, respectively, which are remarkably below the cut-off value (21.3 and 17.4, respectively). 6 weeks after starting abatacept treatment, her prognostic values are the following: MAF$_C$: 20.1 (cut-off 20.3); MAF$_{MRP1}$: 7.8 (cut-off 6.0) and MAF$_{MDR1}$ 12.3 (cut-off: 13.9). During all chekups remarkable improvement was recorded regarding to her disease status.

Patient 2: 61 years old female patient with etanercept (anti-TNF) treatment. Her DAS28 values showed significant decrease during the clinical trial (5.59; 4.58; 2.3; 1.9, respectively). Her baseline MAF$_C$ value was 20.5, which is below the cut-off value. 6 weeks after starting anti-TNF therapy, her MAF$_C$ value was drastically declined (11.5 vs 20.5) which also suggests favorable treatment response. In the same time point, her MAF$_{MRP1}$ and her MAF$_{MDR1}$ values were also significantly below the respective reference values (0.0 and 11.5, respectively). Importantly, her physician also recorded favorable treatment response during the whole study period.

In contrary with Patients 1 and 2, Patient 3 (68 years old woman) showed poor response to abatacept treatment. Regarding to her DAS28 values, no difference was detected during the whole study period (3.06; 3.06; 3.03; 3.03, respectively). Her baseline MAF$_C$ value was remarkably over the cut-off value (22.8 vs 21.3). 6 weeks after starting abatacept treatment, her MAF$_C$ value showed a more robust elevation (24.9) which is over the cut-off value. The same tendency was detected in case of MAF$_{MDR1}$, the 8.3 MAF$_{MDR1}$ value increased to 14.3 which suggests unfavorable treatment outcome. In accordance with the previously mentioned values, her MAF$_{MRP1}$ was also dramatically elevated as compared with the cut-off value (10.6 vs 6.0). In accordance with transporter activity data, no improvement was detected reading to her disease status, thus a tsDMARD treatment would highly be recommended to her.

INDUSTRIAL APPLICABILITY

The invention is useful to provide predictors before the start of the bDMARD therapy and thereby an option to decide about further treatment before symptoms reflect the success of the therapy. As in RA the window of opportunity to apply therapy is limited, the invention is useful to find the appropriate treatment in time.

REFERENCES

Alamanos, Y. and A. A. Drosos (2005). "Epidemiology of adult rheumatoid arthritis." *Autoimmun Rev* 4(3): 130-136.

Aletaha, D., F. Alasti, et al. (2016). "Optimisation of a treat-to-target approach in rheumatoid arthritis: strategies for the 3-month time point." *Ann Rheum Dis* 75(8): 1479-1485.

Bongartz, T., A. J. Sutton, et al. (2006). "Anti-TNF antibody therapy in rheumatoid arthritis and the risk of serious infections and malignancies: systematic review and meta-analysis of rare harmful effects in randomized controlled trials." *JAMA* 295(19): 2275-2285.

Brenol, C. V., J. I. Nava, et al. (2015). "Proper management of rheumatoid arthritis in Latin America. What the guidelines say?" *Clin Rheumatol* 34 Suppl 1: S51-55.

Bystrom, J., F. I. Clanchy, et al. (2017). "Response to Treatment with TNFalpha Inhibitors in Rheumatoid Arthritis Is Associated with High Levels of GM-CSF and GM-CSF(+) T Lymphocytes." *Clin Rev Allergy Immunol* 53(2): 265-276.

Cardiel, M. H., A. Diaz-Borjon, et al. (2014). "Update of the Mexican College of Rheumatology guidelines for the pharmacologic treatment of rheumatoid arthritis." *Reumatol Clin* 10(4): 227-240.

Castilho-Martins, E. A., G. A. Canuto, et al. (2015). "Capillary electrophoresis reveals polyamine metabolism modulation in *Leishmania* (*Leishmania*) *amazonensis* wild type and arginase knockout mutants under arginine starvation." *Electrophoresis*.

Cole, S. P., G. Bhardwaj, et al. (1992). "Overexpression of a transporter gene in a multidrug-resistant human lung cancer cell line." *Science* 258(5088): 1650-1654.

Damiani, D., M. Tiribelli, et al. (2006). "The prognostic value of P-glycoprotein (ABCB) and breast cancer resistance protein (ABCG2) in adults with de novo acute myeloid leukemia with normal karyotype." *Haematologica* 91(6): 825-828.

Deeley, R. G., C. Westlake, et al. (2006). "Transmembrane transport of endo- and xenobiotics by mammalian ATP-binding cassette multidrug resistance proteins." *Physiol Rev* 86(3): 849-899.

Evers, R., G. J. Zaman, et al. (1996). "Basolateral localization and export activity of the human multidrug resistance-associated protein in polarized pig kidney cells." *J Clin Invest* 97(5): 1211-1218.

Felson, D. T., J. S. Smolen, et al. (2011). "American College of Rheumatology/European League against Rheumatism provisional definition of remission in rheumatoid arthritis for clinical trials." *Ann Rheum Dis* 70(3): 404-413.

Flens, M. J., G. J. Zaman, et al. (1996). "Tissue distribution of the multidrug resistance protein." *Am J Pathol* 148(4): 1237-1247.

Fransen, J. and P. L. van Riel (2005). "The Disease Activity Score and the EULAR response criteria." *Clin Exp Rheumatol* 23(5 Suppl 39): S93-99.

Garcia-Carrasco, M., C. Mendoza-Pinto, et al. (2015). "P-glycoprotein in autoimmune rheumatic diseases." *Autoimmun Rev* 14(7): 594-600.

Georges, E., T. Tsuruo, et al. (1993). "Topology of P-glycoprotein as determined by epitope mapping of MRK-16 monoclonal antibody." *J Biol Chem* 268(3): 1792-1798.

Ghandadi, M. and A. Sahebkar (2016). "Interleukin-6: A Critical Cytokine in Cancer Multidrug Resistance." *Curr Pharm Des* 22(5): 518-526.

Gottesman, M. M., T. Fojo, et al. (2002). "Multidrug resistance in cancer: role of ATP-dependent transporters." *Nat Rev Cancer* 2(1): 48-58.

Hipfner, D. R., S. D. Gauldie, et al. (1994). "Detection of the M(r) 190,000 multidrug resistance protein, MRP, with monoclonal antibodies." *Cancer Res* 54(22): 5788-5792.

Kalliokoski, A. and M. Niemi (2009). "Impact of OATP transporters on pharmacokinetics." *Br J Pharmacol* 158(3): 693-705.

Kavanaugh, A., R. M. Fleischmann, et al. (2013). "Clinical, functional and radiographic consequences of achieving stable low disease activity and remission with adalimumab plus methotrexate or methotrexate alone in early rheumatoid arthritis: 26-week results from the randomised, controlled OPTIMA study." *Ann Rheum Dis* 72(1): 64-71.

Lau, C. S., F. Chia, et al. (2015). "APLAR rheumatoid arthritis treatment recommendations." *Int J Rheum Dis* 18(7): 685-713.

Lee, V. W., T. S. Chau, et al. (2010). "Pharmacogenetics of esomeprazole or rabeprazole-based triple therapy in *Helicobacter pylori* eradication in Hong Kong non-ulcer dyspepsia Chinese subjects." *J Clin Pharm Ther* 35(3): 343-350.

Lima, A., R. Azevedo, et al. (2013). "Current approaches for TYMS polymorphisms and their importance in molecular epidemiology and pharmacogenetics." *Pharmacogenomics* 14(11): 1337-1351.

Lima, A., M. Bernardes, et al. (2014). "SLC19A1, SLC46A1 and SLCO1B1 polymorphisms as predictors of methotrexate-related toxicity in Portuguese rheumatoid arthritis patients." *Toxicol Sci* 142(1): 196-209.

Lima, A., J. Monteiro, et al. (2014). "Prediction of methotrexate clinical response in Portuguese rheumatoid arthritis patients: implication of MTHFR r51801133 and ATIC rs4673993 polymorphisms." *Biomed Res* Int 2014: 368681.

Linde, L., J. Sorensen, et al. (2010). "Does clinical remission lead to normalization of EQ-5D in patients with rheumatoid arthritis and is selection of remission criteria important?" *J Rheumatol* 37(2): 285-290.

Marki-Zay, J., K. Tauberne Jakab, et al. (2013). "MDR-ABC transporters: biomarkers in rheumatoid arthritis." *Clin Exp Rheumatol* 31(5): 779-787.

Mercier, C., C. Masseguin, et al. (2004). "Expression of P-glycoprotein (ABCB1) and Mrp1 (ABCC1) in adult rat brain: focus on astrocytes." *Brain Res* 1021(1): 32-40.

Nurmohamed, M. T. and B. A. Dijkmans (2008). "Are biologics more effective than classical disease-modifying antirheumatic drugs?" *Arthritis Res Ther* 10(5): 118.

Picchianti-Diamanti, A., M. M. Rosado, et al. (2014). "P-glycoprotein and drug resistance in systemic autoimmune diseases." *Int J Mol Sci* 15(3): 4965-4976.

Porcelli, L., C. Lemos, et al. (2009). "Intracellular trafficking of MDR transporters and relevance of SNPs." *Curr Top Med Chem* 9(2): 197-208.

Prasad, B., Y. Lai, et al. (2013). "Interindividual variability in the hepatic expression of the human breast cancer resistance protein (BCRP/ABCG2): effect of age, sex, and genotype." *J Pharm Sci* 102(3): 787-793.

Provan, S. A., A. G. Semb, et al. (2011). "Remission is the goal for cardiovascular risk management in patients with rheumatoid arthritis: a cross-sectional comparative study." *Ann Rheum Dis* 70(5): 812-817.

Radner, H., J. S. Smolen, et al. (2014). "Remission in rheumatoid arthritis: benefit over low disease activity in patient-reported outcomes and costs." *Arthritis Res Ther* 16(1): R56.

Rindfleisch, J. A. and D. Muller (2005). "Diagnosis and management of rheumatoid arthritis." *Am Fam Physician* 72(6): 1037-1047.

Romao, V. C., E. M. Vital, et al. (2017). "Right drug, right patient, right time: aspiration or future promise for biologics in rheumatoid arthritis?" *Arthritis Res Ther* 19(1): 239.

Ronaldson, P. T., T. Ashraf, et al. (2010). "Regulation of multidrug resistance protein 1 by tumor necrosis factor alpha in cultured glial cells: involvement of nuclear factor-kappaB and c-Jun N-terminal kinase signaling pathways." *Mol Pharmacol* 77(4): 644-659.

Schett, G., S. Hayer, et al. (2005). "Mechanisms of Disease: the link between RANKL and arthritic bone disease." *Nat Clin Pract Rheumatol* 1(1): 47-54.

Scott, D. L., K. Pugner, et al. (2000). "The links between joint damage and disability in rheumatoid arthritis." *Rheumatology (Oxford)* 39(2): 122-132.

Scott, D. L., F. Wolfe, et al. (2010). "Rheumatoid arthritis." *Lancet* 376(9746): 1094-1108.

Silva, L. C., G. M. Almeida, et al. (2015). "Modulation of the expression of mimivirus-encoded translation-related genes in response to nutrient availability during *Acanthamoeba castellanii* infection." *Front Microbiol* 6: 539.

Smolen, J. S., R. Landewe, et al. (2017). "EULAR recommendations for the management of rheumatoid arthritis with synthetic and biological disease-modifying antirheumatic drugs: 2016 update." *Ann Rheum Dis* 76(6): 960-977.

St-Pierre, M. V., M. A. Serrano, et al. (2000). "Expression of members of the multidrug resistance protein family in human term placenta." *Am J Physiol Regul Integr Comp Physiol* 279(4): R1495-1503.

Telbisz, A., C. Hegedus, et al. (2012). "Antibody binding shift assay for rapid screening of drug interactions with the human ABCG2 multidrug transporter." *Eur J Pharm Sci* 45(1-2): 101-109.

Thiele, K., D. Huscher, et al. (2013). "Performance of the 2011 ACR/EULAR preliminary remission criteria compared with DAS28 remission in unselected patients with rheumatoid arthritis." *Ann Rheum Dis* 72(7): 1194-1199.

Tsujimura, S. and Y. Tanaka (2015). "Disease control by regulation of P-glycoprotein on lymphocytes in patients with rheumatoid arthritis." *World J Exp Med* 5(4): 225-231.

van der Heijde, D. (2012). "Remission by imaging in rheumatoid arthritis: should this be the ultimate goal?" *Ann Rheum Dis* 71 Suppl 2: i89-92.

Vasudevan, S., T. Tsuruo, et al. (1998). "Mode of binding of anti-P-glycoprotein antibody MRK-16 to its antigen. A crystallographic and molecular modeling study." *J Biol Chem* 273(39): 25413-25419.

Verheul, M. K., U. Fearon, et al. (2015). "Biomarkers for rheumatoid and psoriatic arthritis." *Clin Immunol* 161(1): 2-10.

Wijbrandts, C. A. and P. P. Tak (2017). "Prediction of Response to Targeted Treatment in Rheumatoid Arthritis." *Mayo Clin Proc* 92(7): 1129-1143.

Wijnholds, J., E. C. deLange, et al. (2000). "Multidrug resistance protein 1 protects the choroid plexus epithelium and contributes to the blood-cerebrospinal fluid barrier." *J Clin Invest* 105(3): 279-285.

Wollenhaupt, J., K. Albrecht, et al. (2013). "The new 2012 German recommendations for treating rheumatoid arthritis: differences compared to the European standpoint." *Z Rheumatol* 72(1): 6-9.

Zweig, M. H. and G. Campbell (1993). "Receiver-operating characteristic (ROC) plots: a fundamental evaluation tool in clinical medicine." *Clin Chem* 39(4): 561-577.

The invention claimed is:

1. A method for treating a synthetic disease-modifying antirheumatic drug (sDMARD) treated rheumatoid arthritis (RA) patient by assessing the responsiveness of said patient to biological disease-modifying antirheumatic drug therapy (bDMARD therapy), wherein the patient is in need of a switch or modification of the sDMARD therapy and is before or in an initial phase of a bDMARD therapy, wherein the initial phase of the bDMARD therapy is no longer than 8 weeks, said method comprising the steps of providing a biological sample of said sDMARD treated RA patient, said sample comprising CD3$^+$ T-lymphocytes from said patient, obtaining a multidrug transporter activity value by measuring transport activity of MDR1 (ABCB1) in the CD3$^+$ T-lymphocytes of said sDMARD treated RA patient, before or in the initial phase of the bDMARD therapy, by using one or more a detectable, fluorescent substrate of MDR1, said substrate being taken up by CD3$^+$ T-lymphocytes once contacted with them in the biological sample, comparing the multidrug transporter activity value with a pre-determined threshold transporter activity level, wherein the pre-determined threshold transporter activity level is a threshold value for said multidrug transporter activity value and has been determined using the same detectable, fluorescent substrate of MDR1, by measuring or quantifying transport activity of MDR1 in the CD3+ T-lymphocytees in a reference patient group known to be responder to the bDMARD therapy and a reference patient group known to be non-responder to the bDMARD therapy, by using said substrate, and the transport activity values measured in the responder and non-responder patient groups are analysed to find a threshold level which differentiates between responder activity values and non-responder transport activity values, carrying out or continuing the bDMARD therapy when the level of each of the multidrug transporter activity value is not higher than the respective pre-determined threshold transporter activity level, or carrying out another sDMARD therapy or an alternative therapy, when the level of the multidrug transporter activity value is higher than the respective pre-determined threshold transporter activity level.

2. The method of claim 1, wherein the multidrug transporter activity value is obtained by measuring transport activity of one or more multidrug transporters comprising MDR1 and MRP1 in the CD3$^+$ T-lymphocytes of said sDMARD treated RA patient before the bDMARD therapy or in the initial phase thereof by using one or more detectable, fluorescent substrate(s) of MDR1 and MRP1, and comparing the multidrug transporter activity value with a pre-determined threshold transporter activity level, wherein said pre-determined threshold transporter activity level has been determined using the same one or more detectable, fluorescent substrate(s) of MDR1 and MRP1, by measuring or quantifying transport activity of MDR1 and MRP1 in the CD3+ T-lymphocytees in a reference patient group known to be responder to the bDMARD therapy and a reference patient group known to be non-responder to the bDMARD therapy, by using said substrate(s), and the transport activity values measured in the responder and non-responder patient groups are analysed to find a threshold level which differentiates between responder activity values and non-responder transport activity values, carrying out or continuing the bDMARD therapy when the level of the multidrug transporter activity value is not higher than the respective predetermined threshold transporter activity level or carrying out another sDMARD therapy or an alternative therapy, when the level of the multidrug transporter activity value is higher than the respective pre-determined threshold transporter activity level.

3. The method of claim 2 wherein said multidrug transporter activity value is measured with a substrate of both MDR1 and MRP1, the transporter activity comprising activities of both MDR1 and MRP1 and the two transporters are not differentiated by inhibition, whereby a composite transporter MDR1-MRP1 activity value is obtained.

4. The method of claim 2 wherein measuring the transporter activity comprises contacting at least the CD3$^+$ T-lymphocytes in the biological sample with the one or more transporter substrate(s), said substrate being a derivative of a detectable fluorescent compound, and wherein said derivative is taken up by at least the CD3$^+$ T-lymphocytes and is hydrolyzed into said fluorescent compound in cells, wherein said fluorescent compound gets trapped inside said T-lymphocytes, and measuring fluorescence in the CD3$^+$ T-lymphocytes, obtaining the transport activity value from the fluorescence in the CD3$^+$ T-lymphocytes.

5. The method of claim 2, wherein said method comprises carrying out an alternative therapy when the level of said multidrug transporter activity value is above said respective pre-determined threshold transporter activity level, said alternative therapy being a targeted synthetic disease-modifying antirheumatic drug (tsDMARD) therapy.

6. The method of claim 2, wherein the comparing led to carrying out or continuing the bDMARD therapy because the transporter activity value was not higher than the respective pre-determined threshold transporter activity level, said method further comprising repeating the measuring transport activity of one or more multidrug transporters comprising MDR1 and MRP1 in the CD3$^+$ T-lymphocytes of said sDMARD treated RA patient at 4 to 7 weeks of the bDMARD therapy.

7. The method of claim 1 wherein the transport activity values measured in the responder and non-responder patient groups are statistically analysed as distributions to find a threshold level which differentiates between responder transport activity values and non-responder transport activity values.

8. The method of claim 1 wherein the substrate is a detectable fluorescent ester compound, and the activity is quantified as a multidrug activity factor (MAF).

9. The method of claim 1, wherein said bDMARD therapy is selected from the group consisting of anti-TNF therapy, T-cell activation inhibitor therapy, B lymphocyte depletion therapy, and anti-IL6 therapy.

10. The method of claim 1, wherein measuring the transporter activity comprises contacting at least the CD3$^+$ T-lymphocytes in the biological sample with the one or more transporter substrate(s), said substrate being a derivative of a detectable fluorescent compound, and wherein said derivative is taken up by at least the CD3$^+$ T-lymphocytes and is hydrolyzed into said fluorescent compound in cells, wherein said fluorescent compound gets trapped inside said T-lymphocytes, and measuring fluorescence in the CD3$^+$ T-lymphocytes, obtaining the transport activity value from the fluorescence in the CD3$^+$ T-lymphocytes.

11. The method of claim 1, wherein the sDMARD is a "csDMARD" ("conventional synthetic disease-modifying antirheumatic drug"), selected from the group of compounds consisting of azathioprine, cyclophosphamide, cyclosporine, hydroxychloroquine sulfate, leflunomide, methotrexate, mycophenolate mofetil, sulfasalazine, glucocorticoids, chloroquine and salazopryne.

12. The method of claim 1, wherein said detectable, fluorescent substrate of MDR1 is in the form of a kit, wherein said kit comprises a label for CD3+ T-lymphocytes.

13. The method of claim 12, wherein the multidrug transporter activity value(s) is/are value is obtained by measuring transport activity of both MDR1 and MRP1, or by measuring a composite MDR1 and MRP1 transport activity, in the CD3$^+$ T-lymphocytes of said sDMARD treated RA patient before the bDMARD therapy or in the initial phase thereof, by using a detectable, fluorescent substrate of MDR1 and MRP1, wherein the detectable, fluorescent substrate for the measuring MDR1 and MRP1 transport activities or a composite MDR1 and MRP1 transport activity is in the form of a kit, said substrate being taken up by leukocytes, once the CD3$^+$ T-lymphocytes are contacted with the reagents in the biological sample, and the CD3$^+$ T-lymphocytes are labelled wherein said label for CD3$^+$ T-lymphocytes is also in the form of a kit.

14. The method of claim 12, wherein measuring the transporter activity comprises contacting at least the CD3$^+$ T-lymphocytes in the biological sample with the detectable, fluorescent substrate, said substrate being a derivative of a detectable fluorescent compound, and wherein said derivative is taken up by at least the CD3$^+$ T-lymphocytes and is hydrolyzed into said fluorescent compound in cells, wherein said fluorescent compound gets trapped inside said T-lymphocytes, measuring fluorescence in the CD3$^+$ T-lymphocytes, and obtaining the multidrug transport activity value from the fluorescence in the CD3$^+$ T-lymphocytes.

15. The method of claim 12, wherein the substrate is a detectable fluorescent ester compound, and the activity is quantified as a multidrug activity factor (MAF).

16. The method of claim 1, wherein said method comprises carrying out the alternative therapy when the level of said multidrug transporter activity value measured is higher than the respective threshold level, said alternative therapy being a targeted synthetic disease-modifying antirheumatic drug (tsDMARD) therapy.

17. An in vitro diagnostic method for assessing the responsiveness of a synthetic disease-modifying antirheumatic drug (sDMARD) treated RA patient to biological synthetic disease-modifying antirheumatic drug therapy (bDMARD therapy), wherein the patient is in need of a switch or modification of the sDMARD therapy and is before or in an initial phase of a bDMARD therapy, wherein the initial phase of the bDMARD therapy is no longer than 8 weeks, said method comprising the steps of providing a biological sample of said sDMARD treated RA patient, said sample comprising CD3$^+$ T-lymphocytes from said patient, obtaining one or more multidrug transporter activity value(s) by measuring transport activity of MDR1 (ABCB1) in the CD3+ T-lymphocytes of said sDMARD treated RA patient, before or in the initial phase of the bDMARD therapy, by using one or more detectable, fluorescent substrate(s) of MDR1, said substrate(s) being taken up by CD3$^+$ T-lymphocytes once contacted with them in a biological sample, comparing the one or more transporter activity value(s) with one or more pre-determined threshold transporter activity level(s), wherein each pre-determined threshold transporter activity level is a threshold value for said one or more multidrug transporter activity value(s) and has been determined using the same one or more detectable, fluorescent substrate(s) of MDR1 by, measuring or quantifying transport activity of MDR1 in the CD3+ T-lymphocytes in a reference patient group known to be responder to the bDMARD therapy and a reference patient group known to be non-responder to the bDMARD therapy, by using said substrate(s), and the transport activity values measured in the responder and non-responder patient groups are analysed to find a threshold level which differentiates between responder transport activity values and non-responder transport activity values, considering said RA patient as a non-responder to the bDMARD therapy and therefore suitable/eligible for another sDMARD therapy, or an alternative therapy, when the level of said one or more multidrug transporter activity value(s) measured is above said pre-determined threshold transporter activity level, and considering said RA patient as a responder to and therefore suitable for carrying out or continuing the bDMARD therapy when the level of each multidrug transporter activity value is not higher than said pre-determined threshold transporter activity level.

18. The in vitro method of claim 17, wherein said bDMARD therapy is selected from the group consisting of anti-TNF therapy, T-cell activation inhibitor therapy, B lymphocyte depletion therapy, and anti-IL6 therapy.

19. The in vitro method of claim 17, wherein measuring the transporter activity comprises contacting at least the CD3$^+$ T-lymphocytes in the biological sample with the one or more transporter substrate(s), said substrate being a derivative of a detectable fluorescent compound, and wherein said derivative is taken up by at least the CD3$^+$ T-lymphocytes and is hydrolyzed into said fluorescent compound in cells, wherein said fluorescent compound gets trapped inside said T-lymphocytes, and measuring fluorescence in the CD3$^+$ T-lymphocytes, obtaining the transport activity value from the fluorescence in the CD3$^+$ T-lymphocytes.

20. The in vitro method of claim 17, wherein the one or more multidrug transporter activity value is/are obtained by measuring transport activity of both MDR1 and MRP1 in the CD3$^+$ T-lymphocytes of said sDMARD treated RA patient before the bDMARD therapy or in the initial phase thereof by using one or more detectable, fluorescent substrate(s) of MDR1 and MRP1, and the transporter activity value is compared with a pre-determined threshold transporter activity level, wherein said pre-determined threshold transporter activity level has been determined using the same one or more detectable, fluorescent substrate(s) of MDR1 and MRP1, by measuring or quantifying transport activity of MDR1 and MRP1 in the CD3+ T-lymphocytes in a reference patient group known to be responder to the bDMARD therapy and a reference patient group known to be non-responder to the bDMARD therapy, by using said substrate(s), and the transport activity values measured in the responder and non-responder patient groups are analysed to find a threshold level which differentiates between responder transport activity values and non-responder transport activity values, considering said RA patient as a non-responder to the bDMARD therapy when the level of the MDR1 and MRP1 transporter activity value is above said pre-determined threshold transporter activity level, and considering said RA patient as a responder to the bDMARD therapy when the level of the MDR1 and MRP1 transporter activity value is not higher than said pre-determined threshold transporter activity level.

21. The in vitro method of claim 17 wherein said threshold transporter activity level has been determined by measuring the transport activity of said one or more multidrug transporters in the CD3$^+$ T-lymphocytes in a reference patient group known to be responder to the bDMARD therapy and a further reference patient group known to be non-responder to the bDMARD therapy, and the transport activity values measured in the responder and non-responder patient groups are statistically analysed as distributions to find a threshold level which differentiates between responder transport activity values and non-responder transport activity values.

22. The in vitro diagnostic method of claim 17 wherein the substrate is a detectable fluorescent ester compound, and the activity is quantified as a multidrug activity factor (MAF).

23. The method of claim 17, wherein said method comprises carrying out the alternative therapy, when the level of said one or more transporter activity value(s) measured is above said respective threshold level, said alternative therapy being a targeted synthetic disease-modifying antirheumatic drug (tsDMARD) therapy.

* * * * *